US012702132B2

(12) United States Patent
Kleinman

(10) Patent No.: US 12,702,132 B2
(45) Date of Patent: Aug. 11, 2026

(54) METHODS FOR USING BIOADHESIVE AND STERIC INTERACTIONS OF COPOLYMERS WITH AT LEAST TWO MOIETIES TO MINIMIZE ADVERSE EFFECTS MEDIATED BY EXTERNAL INFLUENCES ON CELL, TISSUE, ORGAN SYSTEM, AND ORGANISM BIOLOGY

(71) Applicant: Calm Water Therapeutics LLC, Rochester, NY (US)

(72) Inventor: David Maxwell Kleinman, Rochester, NY (US)

(73) Assignee: Calm Water Therapeutics LLC, Rochester, NY (US)

( * ) Notice: Subject to any disclaimer, the term of this patent is extended or adjusted under 35 U.S.C. 154(b) by 598 days.

(21) Appl. No.: 18/053,316

(22) Filed: Nov. 7, 2022

(65) Prior Publication Data

US 2023/0201251 A1 Jun. 29, 2023

Related U.S. Application Data

(63) Continuation of application No. PCT/US2021/031266, filed on May 7, 2021.

(60) Provisional application No. 63/021,277, filed on May 7, 2020.

(51) Int. Cl.

| | |
|---|---|
| ***A01N 33/08*** | (2006.01) |
| ***A61K 31/785*** | (2006.01) |
| ***A61K 47/68*** | (2017.01) |
| ***A61P 31/14*** | (2006.01) |

(52) U.S. Cl.

CPC ............ *A01N 33/08* (2013.01); *A61K 31/785* (2013.01); *A61K 47/68031* (2023.08); *A61K 47/6849* (2017.08); *A61P 31/14* (2018.01)

(58) Field of Classification Search

None

See application file for complete search history.

(56) References Cited

U.S. PATENT DOCUMENTS

| | | | |
|---|---|---|---|
| 5,578,442 A | 11/1996 | Desai et al. | |
| 5,834,556 A | 11/1998 | Desai et al. | |
| 8,802,075 B2 | 8/2014 | Cooper et al. | |
| 9,005,596 B2 | 4/2015 | Cooper et al. | |
| 9,283,248 B2 | 3/2016 | Cooper et al. | |
| 9,295,693 B2 | 3/2016 | Cooper et al. | |
| 9,884,074 B2 | 2/2018 | Cooper et al. | |
| 2004/0181172 A1 | 9/2004 | Carney et al. | |
| 2018/0161363 A1* | 6/2018 | Cooper | A61K 9/5031 |

FOREIGN PATENT DOCUMENTS

| | | |
|---|---|---|
| CN | 102395378 A | 3/2012 |
| JP | 2016-516048 A | 6/2016 |

OTHER PUBLICATIONS

PLL-g-PEG decreases said damage or adverse effects to said nonneoplastic cells (Year: 2026).*
PLL-g-PEG (Year: 2026).*
Lan et al.; Structure of the SARS-COV-2 spike receptor-binding domain bound to the ACE2 receptor; Nature, vol. 581, No. 7807, 2020, 215-220. (Year: 2020) (Year: 2020).*
Ruiz-Taylor et al.; Monolayers of derivatized poly(L-lysine)-grafted poly(ethylene glycol) on metal oxides as a class of biomolecular interfaces; PNAS; vol. 98, No. 3, (2001), 852-857 (Year: 2001).*
Japan Patent Office, Notice of Reasons for Refusal for Japanese Patent Application No. 2022-567891, dated Mar. 18, 2025, 6 pages.
European Office Action for European Patent Application No. 21799717.0, dated Aug. 4, 2025, 3 pages.
Chinese Office Action for Chinese Patent Application No. 202180045498.1, dated Jan. 4, 2026, with English translation, 14 pages.
Ando, R., et al. "Tissue factor expression in human pterygium." Mol Vis. Jan. 8, 2011;17:63-9.
Aschauer, J., et al. "Corneal Toxicity Associated With Belantamab Mafodotin Is Not Restricted to the Epithelium: Neuropathy Studied With Confocal Microscopy." American Journal of Ophthalmology 242 (2022): 116-124.
Chiang, J., et al. "Corneal nerve changes following treatment with neurotoxic anticancer drugs." The Ocular Surface 21 (2021): 221-237.
Corbelli, E., et al. "Ocular toxicity of mirvetuximab." Cornea 38.2 (2019): 229-232.
Dutta, D., et al. "Search for inhibitors of endocytosis: Intended specificity and unintended consequences." Cell Logist. Oct. 1, 2012;2(4):203-208.
Farooq, A., et al. "Corneal epithelial findings in patients with multiple myeloma treated with antibody-drug conjugate belantamab mafodotin in the pivotal, randomized, DREAMM-2 study." Ophthalmology and Therapy 9.4 (2020): 889-911.
International Search Report and Written Opinion for International Application No. PCT/US2021/031266, mailed Oct. 15, 2021, 15 pages.

(Continued)

*Primary Examiner* — Robert A Wax
*Assistant Examiner* — John W Lippert, III
(74) *Attorney, Agent, or Firm* — Nutter McClennen & Fish LLP

(57) ABSTRACT

Methods for using bioadhesive and stearic interactions specific to copolymers with at least two moieties, to minimize adverse effects mediated by external influences on cell, tissue, organ system, and organism biology. Copolymers have bioadhesive properties driven by electrostatic and hydrophobic interactions and passivation though hydrophilic moieties. These copolymers are useful for reducing rates of viral infectivity in target cells, and in reducing host morbidity. These copolymers are useful for reducing ADC related toxicity including corneal epithelial toxicity. Formulations of these copolymers are safe and well tolerated. Epithelial cells and surfaces including precursor or stem cell corneal epithelial cells are treated with these copolymers to confer utility and benefit.

10 Claims, 5 Drawing Sheets

Specification includes a Sequence Listing.

(56) References Cited

OTHER PUBLICATIONS

Kleinman, D., et al. "PLL-g-PEG inhibits antibody-drug conjugate uptake into human corneal epithelial cells in vitro." Investigative Ophthalmology & Visual Science 63.7 (2022): 3239-A0274.
Lan, J., et al. "Structure of the SARS-CoV-2 spike receptor-binding domain bound to the ACE2 receptor." Mar. 30, 2020, Nature vol. 581, No. 7807, pp. 215-220.
Lin, H., et al. "Identification of novel macropinocytosis inhibitors using a rational screen of Food and Drug Administration-approved drugs." British journal of pharmacology 175.18 (2018): 3640-3655.
Lühmann, T., et al. "Cellular uptake and intracellular pathways of PLL-g-PEG-DNA nanoparticles." Bioconjugate chemistry 19.9 (2008): 1907-1916.
Marquant, K., et al. "Corneal in vivo confocal microscopy to detect belantamab mafodotin-induced ocular toxicity early and adjust the dose accordingly: a case report." Journal of Hematology & Oncology 14.1 (2021): 1-8.
Matlock, HG., et al. "Pathogenic Role of PPARα Downregulation in Corneal Nerve Degeneration and Impaired Corneal Sensitivity in Diabetes." Diabetes. Jun. 2020;69(6):1279-1291.
Mencucci, R., et al. "Corneal Findings Associated to Belantamab-Mafodotin (Belamaf) Use in a Series of Patients Examined Longitudinally by Means of Advanced Corneal Imaging." Journal of Clinical Medicine 11.10 (2022): 2884.
Nakamura, Y., et al. "Functional role of PPARδ in corneal epithelial wound healing." The American journal of pathology 180.2 (2012): 583-598.
Renukuntla, J., et al. "Expression of Folate Receptor (FR-alpha) and Proton Coupled Folate Transporter (PCFT) on RPCEC and HCEC Cell Line." Investigative Ophthalmology & Visual Science 59.9 (2018): 3852-3852.
Ringvold, H.C., et al. "Protein kinase C as regulator of vascular smooth muscle function and potential target in vascular disorders." Advances in pharmacology 78 (2017): 203-301.
Sawhney, A., et al. "Poly(ethylene oxide)-graft-poly(L-lysine) copolymers to enhance the biocompatibility of poly(L- ysine)-alginate microcapsule membranes," Biomaterials vol. 13, Issue 12, 1992, pp. 863-870.
Takahashi, J., et al. "Synchronous intracellular delivery of EGFR-targeted antibody-drug conjugates by p38-mediated non-canonical endocytosis." Sci Rep 12, 11561 (2022).
Zhao, H., et al. "Modulation of Macropinocytosis-Mediated Internalization Decreases Ocular Toxicity of Antibody-Drug Conjugates," Cancer Res Apr. 15, 2018; 78 (8), pp. 2115-2126.
Chinese Office Action for Chinese Patent Application No. 202180045498.1, dated Oct. 29, 2024 with English translation, 10 pages.
Japanese Office Action for Japanese Patent Application No. 2022-567891, dated Jun. 24, 2024, with English translation, 14 pages.
Nemeth, A., et al., " Antibiotic-induced release of small extracellular vesicles (exosomes) with surface-associated DNA." Sci Rep 7, 8202 (2017), 16 pages.
Park, S., et al., "Micropatterned Viral Membrane Clusters for Antiviral Drug Evaluation. ACS Appl Mater Interfaces." Apr. 17, 2019;11(15): 13984-13990.
Radovic-Moreno, AF., et al., "Surface charge-switching polymeric nanoparticles for bacterial cell wall-targeted delivery of antibiotics." ACS Nano. May 2, 20122;6(5):4279-4287.
Wattendorf, U., et al., "Mannose-based molecular patterns on stealth microspheres for receptor-specific targeting of human antigen-presenting cells." Langmuir. Oct. 21, 2008;24(20):11790-11802.
Japanese Notice of Reasons for Refusal for Japanese Patent Application No. 2022-567891, dated Mar. 18, 2025 with English translation, 6 pages.
Chinese Office Action for Chinese Patent Application No. 202180045498.1, dated Jul. 7, 2025 with English translation, 6 pages.
Extended European Search Report for European Application No. 21799717.0 dated May 2, 2024, 5 pages.
Sapsford, K., et al., "Functionalizing Nanoparticles with Biological Molecules: Developing Chemistries that Facilitate Nanotechnology", Chemical Reviews, vol. 113, No. 3, Mar. 13, 2013, pp. 1904-2074.
Suo, Z., et al., "Efficient Immobilization and Patterning of Live Bacterial Cells", Langmuir, vol. 24, No. 8, Apr. 1, 2008, pp. 4161-4167.
Canadian Office Action for Canadian Patent Application No. 3,182,679, dated Apr. 17, 2026, 4 pages.

* cited by examiner

METHODS FOR USING BIOADHESIVE AND STERIC INTERACTIONS OF COPOLYMERS WITH AT LEAST TWO MOIETIES TO MINIMIZE ADVERSE EFFECTS MEDIATED BY EXTERNAL INFLUENCES ON CELL, TISSUE, ORGAN SYSTEM, AND ORGANISM BIOLOGY

PRIORITY

This application is a Continuation application of International Application No. PCT/US2021/031266, filed May 7, 2021, which claims the benefit of U.S. provisional application No. 63/021,277, filed May 7, 2020, the contents of which are incorporated herein in their entirety.

SEQUENCE LISTING

The instant application contains a Sequence Listing which has been submitted via EFS-Web and is hereby incorporated by reference in its entirety. Said ASCII copy, created on Nov. 7, 2022, is named 3905-11003-seq-listing.xml and is 3721b in size.

FIELD OF THE INVENTION

The present invention provides a method for addressing serious problems currently encountered in the biomedical field by utilizing bioadhesive and passivation copolymers (containing a charged or hydrophobic moiety and a passivation hydrophilic moiety) to improve cellular, tissue, organ and mammalian health. Specifically, the field of this invention relates to the prevention, attenuation, reduction, or treatment of viral infections. And specifically, the field of this invention relates to the prevention, attenuation, reduction, or treatment of drug related toxicities associated with antibody-drug conjugates (ADCs) and their toxic payloads. "ADC" will be used frequently herein to represent an antibody-drug conjugate therapeutic. ADCs are complex molecules composed of an antibody linked to a biologically active cytotoxic (anticancer) payload or drug. Antibody-drug conjugates may be types of bioconjugates and immunoconjugates. "ADC" can refer to a host of different antibody-drug conjugates herein. ADCs combine targeting capabilities inherent to monoclonal antibodies with the cancer-fighting ability of cytotoxic agents. They are often designed to discriminate between healthy and diseased cells or tissue.

The viral infection specifically of focus here is SARS-CoV-2 infectivity. However, the key development is that the effect is useful for new viruses such that stearic and electrostatic interactions can inhibit the infectivity of a novel virus into a cell, tissue or organism for which host immunity has not yet developed or for which targeted antibody or antiviral therapy are not yet available. In other words, this effect is broad, effective and nonspecific. New viruses are amenable to treatment with this approach.

The ADC toxicity amelioration method is specifically related to off target entry of ADC's into non neoplastic cells and the adverse events associated with inhibiting cellular processes mediated by the ADC payload. Neoplastic cells are cancer cells. The ADC's are used to treat cancer or oncologic disease of one or many organ systems or cell types, including but not limited to renal cell cancers, leukemias, lymphomas, myelomas, lung cancer, prostate cancer, uterine or cervical cancer, breast cancer, bladder cancer, colon cancer, esophageal cancer, liver cancer, Hodgkin's disease, ovarian cancer, pancreatic cancer, rectal cancer, skin cancer, small bowel cancer, solid tumors, stomach cancer, white blood cell cancers, urethral cancer, mesenteric lymphadenitis. Any or all cancers here named and those unnamed can be combined with any claim for a specific invention with an ADC targeting such a cancerous cell or tissue.

Specifically, macropinocytosis mediated toxicity is inhibited, reduced, and limited via the steric and electrostatic interferences that take effect at the molecule-cellular-tissue (inclusive or isolated) level where the surface of a cell or tissue interacts with its local microenvironment. Cells include, but are not limited to limbal stem cells, transient amplifying cells, transient amplifying cells daughter cells, basal epithelial cells, wing cells, and corneal epithelial cells and differentiated corneal epithelial cells.

The primary underlying polymeric structure most useful (but not the only useful embodiment) in both settings is a cationic graft copolymer. The base structure includes a cationic backbone and grafted hydrophilic side chains. A prime example of such a polymer is poly(L)lysine graft (poly)ethylene glycol. Other molecular structures also accomplish the interactions necessary to confer benefits. Other polymers can use charge, hydrophobic and passivation moieties to accomplish these effects and are addressed herein. The treatment method is through the application to a cell, tissue, organ, organism, or mammal of the aforementioned polymer (whether in solution or not) in an amount and for a duration effective to accomplish the intended beneficial effect.

Thus, there is a need to reduce the severity and risks related to new viral disease spreading in human populations and affecting human health.

Further there is a need to reduce the negative impacts related to antibody-drug conjugates, specifically corneal epithelial toxicity.

BACKGROUND OF THE INVENTION

Cationic graft copolymers have demonstrated utility in coating non-biologic surfaces in vitro, in coating medical devices, and for treating dry eye. One example of an effective cationic graft copolymer is Poly(L-lysine)-graft-poly(ethylene glycol)(PLL-g-PEG). PLL-g-PEG is a water soluble co-polymer consisting of a poly(L-lysine) backbone and poly(ethylene glycol) side chains (Sawhney et al. Biomaterials 1992 13:863-870). The PLL chain, which carries multiple positive charges, spontaneously adsorbs onto negatively charged surfaces while PEG is a hydrophilic polymer which serves as a non-binding domain. The PEG moiety passivates a surface while the PLL moiety adheres via electrostatic interaction at the cell membrane or on other charged components of antibodies, viruses, or viral proteins. PLL-g-PEG has been used to passivate in vitro surfaces, experimentally coat medical devices, and has been used as an eye drop for dry eye to lubricate the eye and stabilize the tear film. This invention which goes far beyond the treatment of dry eye is the first identified approach to directly ameliorating ADC corneal toxicity due to tubulin inhibitors among other cytotoxic payloads.

The role of cationic graft copolymers, in particular PLL-g-PEG, in inhibiting viral infectivity and or ADC-related toxicity has neither been considered, studied or reduced to practice prior to this invention. Similarly effective polymeric molecules have also neither been studied or reduced to practice to Applicant's knowledge in these regards prior to this invention. There are multiple configurations of cationic graft copolymers effective in inhibiting viral infectivity and/or ADC-related toxicity. These alternative molecular approaches are considered and addressed herein.

SUMMARY OF THE INVENTION

An aspect of the present invention relates to a method for preventing or reducing viral infectivity and viral load exposure and thereby decreasing morbidity and mortality with viral infections such as SARS-CoV-2 and other viruses, in particular novel viruses. Charged graft copolymers are safe and effective when applied to at-risk cells and tissues to prevent or reduce infectivity.

An aspect of the present invention relates to a method for preventing or reducing ADC-related drug toxicity to off-target cells and tissue. In particular, the invention is a method to reduce the severity of corneal epithelial cell toxicity in the setting of ADC therapy. Charged graft copolymers are safe and effective when applied to at risk cells and tissues to prevent or reduce ADC-related corneal toxicity. Exposure of human corneal epithelial cells including basal epithelial cells as well as their precursors, wing cells and superficial epithelial cells to the cytotoxic payload carried by an ADC are reduced through the utilization of a treatment with cationic graft copolymers. The exposure of epithelial cells to an effective amount of the graft copolymer in solution is effective at reducing the severity of corneal epithelial toxicity. The reduction in severity can be noted on examination findings as a reduction in the microcyst-like epithelial keratopathy, less severe superficial punctate staining, lower rates of epithelial abnormalities, fewer ophthalmic adverse events, reduced rates of decreased visual acuity, fewer complaints of ocular irritation and blurry vision.

One aspect of the invention disclosed herein is a method for decreasing viral infectivity by treating tissues that are involved with transfection with an effective amount of a graft or block copolymer with either cationic, hydrophobic, or anionic moieties and a hydrophilic passivation moiety. In one embodiment of the method, the copolymer is PLL-g-PEG. In another embodiment of the method, the graft co-polymer of said formulation comprises a cationic backbone and side chains that are water soluble and non-ionic. In another embodiment of the method, the block co-polymer of said formulation comprises at least one cationic block and at least one water soluble and non-ionic block. In another embodiment of the method, the block co-polymer of said formulation comprises at least one block which is hydrophobic and at least one block which is water soluble and anionic, cationic or non-ionic. In any of the above embodiments, the biological surface to which the formulation of copolymer is administered is a mucous membrane selected from ocular mucosa, oral mucosa, nasal mucosa and respiratory tract mucosa, respiratory tract epithelium, genitourinary mucosa, gastrointestinal mucosa of a subject. In any of the above embodiments, the biological surface to which the formulation of copolymer is administered is a surface of an eye. In any of the above embodiments, the viral infection is selected from coronaviruses, influenzas viruses, Ebola viruses, and novel viruses transmitted through mucous membrane exposure, including, but not limited to the virus is SARS-COV-2. In any of the above embodiments, the graft co-polymer or block co-polymer of said formulation comprises 0.001 to 40% of said formulation. In any of the above embodiments, the graft co-polymer or block co-polymer of said formulation comprises 0.1 to 10% of said formulation. In any of the above embodiments, the passivation effect is based on interference with the SARS-Cov-2 spike protein and ACE2 receptor on at-risk cells. In any of the above embodiments, the therapeutic effect is a general steric inhibition.

In a second aspect of the invention there is disclosed herein a method to decease the adverse events associated with antibody-drug conjugate usage where an off-target uptake pathway that is causing damage to nonneoplastic cells, by applying an effective amount of a copolymer with electrostatic and steric mediating properties applied to cells that are affected by said toxicity. In one embodiment of this aspect, the copolymer is selected from cationic graft, cationic block, hydrophobic graft, hydrophobic block, anionic graft, and anionic block copolymers. In one embodiment of this aspect, the copolymer is formulated in one or more of the following approaches: powders, solutions, suspensions, topical preparations, intravenous preparations, oral preparations, oral rinses, nasal sprays, eye drops. In one embodiment of this aspect, the percentage of the copolymer solution is at minimum 0.01% by weight. In one embodiment of this aspect, the percentage of the copolymer solution is at maximum 40% by weight for solutions and suspensions. In one embodiment of this aspect, the copolymer is PLL-g-PEG. In one embodiment of this aspect, the copolymer is selected from the list of combinations described in the application supra.

In one component of the ophthalmic aspects of this invention, benefit can be seen with topical ophthalmic therapy with co-polymer containing ophthalmic drug products and/or over-the-counter formulations containing the co-polymer's described herein at a frequency of once daily use (one drop per day per eye), twice daily (two drops per day per eye), thrice or three times daily (three drops per day per eye), four times daily (four drops per day per eye), or up to every hour or more frequent dosage. Dosage may be infrequent as well, at one time per day per affected eye or less. Dosing may be as needed or pro ranata, as well. The range of dosing frequency needs may be patient and ADC dependent.

In another aspect of the invention there is disclosed herein, a method to decrease ADC related corneal epithelial toxicity by administering a copolymer with bioadhesive and passivation components to cells at risk of off target drug uptake. In one embodiment of this aspect, the copolymer is applied to corneal and conjunctival epithelial cells. In one embodiment of this aspect, the copolymer is PLL-g-PEG. In one embodiment of this aspect, the formulation is a solution for delivery to the subconjunctival space.

In another aspect of the invention there is disclosed herein, a method to decease the adverse events associated with antibody-drug conjugate usage in a human whereby an effective amount of a copolymer with electrostatic and steric mediating properties is applied to cells that are involved in said adverse events. In one embodiment of this aspect, the copolymer is selected from cationic graft, cationic block, hydrophobic graft, hydrophobic block, anionic graft, and anionic block copolymers. In one embodiment of this aspect, the copolymer is selected from polymers in this disclosure herein.

In another aspect of the invention there is disclosed herein, a method to decrease microcyst-like epithelial toxicity associated with cytotoxins cleaved from ADC's by applying to corneal epithelial cells an effective amount of a copolymer with bioadherence and passivation properties, including a graft or block copolymer with either cationic, hydrophobic, or anionic moieties and a hydrophilic moiety which may serve as a passivation moiety. In one embodiment of this aspect, the copolymer is PLL-g-PEG.

In another aspect of the invention there is disclosed herein, a method for decreasing rates and severity of ocular adverse events associated with ADC use by delivering to the eye a copolymer with bioadhesive and passivation moieties including a graft or block copolymer with either cationic, hydrophobic, or anionic moieties and a hydrophilic passivation moiety, prior to initiation of systemic ADC therapy.

Ocular adverse events may include but are not limited to corneal epithelial cell death, superficial punctate keratopathy or keratitis, corneal scarring, corneal infections, micro-cyst like keratopathies, corneal cell injury, corneal cell apoptosis, ocular irritation, ocular foreign body sensation, blurred vision, painful eyes, trouble with vision-related tasks, photophobia, keratopathies, and corneal epitheliopathies.

In another aspect of the invention there is disclosed herein, a method for improving signs and symptoms of ocular adverse events associated with ADC use by delivering to the eye a copolymer with bioadhesive and passivation moieties, including a graft or block copolymer with either cationic, hydrophobic, or anionic moieties and a hydrophilic passivation moiety, after initiation of systemic ADC therapy. Signs and symptoms include(s) visual acuity-related symptoms, visual blur, irritation, redness, and eye-exam findings, but is not limited to these specific signs and symptoms. Vision will be better in co-polymer formulation treated eyes.

In another aspect of the invention there is disclosed herein, a method for reduction of a superficial punctate keratopathy or keratitis associated with ADC use by delivering to the eye a copolymer with bioadhesive and passivation moieties, including a graft or block copolymer with either cationic, hydrophobic, or anionic moieties and a hydrophilic passivation moiety, associated with the initiation of systemic ADC therapy. Deliver may be before, concurrent to, or after initiation of ADC therapy. The benefit is similar for this topical ophthalmic therapy when used with other cornea-toxic drugs mentioned herein. In other words, the specification herein supports claims of benefit for this copolymer approach broadly, addressing systemic or topical drug or drug products with known or anticipated cornea-toxicity or ocular adverse events particularly those associated with ADC.

Reducing risks of corneal infection are a benefit to co-polymer-based topical therapy in this setting.

In another aspect of the invention there is disclosed herein, a method to reduce ADC uptake into corneal epithelial cells (whether in culture, laboratory models, or in vivo) by exposing said cells to a copolymer with bioadhesive and passivation moieties, including a graft or block copolymer with either cationic, hydrophobic, or anionic moieties and a hydrophilic passivation moiety, prior to exposure to the ADC.

In another aspect of the invention there is disclosed herein, a method to reduce ADC uptake into corneal epithelial cells by exposing said cells to a copolymer with bioadhesive and passivation moieties, including a graft or block copolymer with either cationic, hydrophobic, or anionic moieties and a hydrophilic passivation moiety, after exposure to the ADC.

In another aspect of the invention there is disclosed herein, a method to reduce ADC uptake by macropinocytosis (or pinocytosis more generally) into corneal epithelial cells by exposing said cells to a copolymer with bioadhesive and passivation moieties, including a graft or block copolymer with either cationic, hydrophobic, or anionic moieties and a hydrophilic passivation moiety, prior to or subsequent to exposure to the ADC, using a formulation with an effective percentage based on weight/weight calculations of said copolymer.

In another aspect of the invention there is disclosed herein, a method to reduce ocular adverse events associated with ADC's by treating a patient with a copolymer with bioadhesive and passivation moieties, including a graft or block copolymer with either cationic, hydrophobic, or anionic moieties and a hydrophilic passivation moiety, using an amount to be efficacious. Treatment is local in some embodiments.

In another aspect of the invention there is disclosed herein, a method of using copolymers demonstrating electrostatic and stearic interactions at the cellular level, including a graft or block copolymer with either cationic, hydrophobic, or anionic moieties and a hydrophilic passivation moiety, to minimize adverse effects caused by exposure of those cells to factors including SARS-Cov-2, novel viruses, viruses in the setting of an epidemic, ADC's with cytotoxic payloads which can lead to human pathology and morbidity.

In another aspect of the invention there is disclosed herein, a method to reduce ocular toxicity due to systemic exposure of a human to ADC's with tubulin disruptors as the payload by treating the eye with an effective amount of cationic graft copolymer formulation, including a graft or block copolymer with either cationic, hydrophobic, or anionic moieties and a hydrophilic passivation moiety. In one embodiment of this aspect, the cationic graft copolymer is PLL-g-PEG. In one embodiment of this aspect, the treatment is through an eye drop formulation. In one embodiment of this aspect, the formulation is unpreserved. In one embodiment of this aspect, the cationic graft copolymer is PLL-g-PEG in a concentration in an eye drop formulation in a weight/weight range from 0.01% to 5%. In one embodiment of this aspect, a less toxic preservatives selected from: sodium perborate, stabilized oxychloro complex, disappearing preservatives, hydrogen peroxide based preservatives.

In another aspect of the invention there is disclosed herein, a method to reduce dose holds and dose reductions of ADC's in the treatment of human malignancy by reducing corneal adverse events and mitigating ocular safety concerns through a PLL-g-PEG eye drop formulation applied to the eye in an effective amount in an at-risk patient. In another embodiment of this invention, ocular toxicity can be mitigated with local treatment with a copolymer, including a graft or block copolymer with either cationic, hydrophobic, or anionic moieties and a hydrophilic passivation moiety, when said toxicity is due to tear secretion of a cytotoxin and secondary effects on the corneal epithelium. Another aspect is utilizing methods described herein to reduce the risk of poor outcomes or a worse course due to corneal drug related toxicity selected from the effects of: decreasing rates of epithelial erosions, decreasing rates of corneal ulcers, decreasing rates of corneal epitheliopathy, decreasing rates of punctate epitheliopathy, decreasing rates of superficial corneal changes, decreasing rates of corneal stromal inflammation or other changes, decreasing rates of secondary bacterial infection.

For the purposes herein, "adversely affected" may mean but is not limited to any alteration from normal physiology and cell or tissue or organ or organism function, including but not limited to reduced cell survival, initiation of apoptosis, reduced proliferative capacity for cells that normally divide, reduced and improper cell adhesion and migration, alterations in adherence and junctional connections including tight junctions, inflammatory responses to cells or tissue, changes to cell metabolism and catabolism, cell bystander damage, changes that lead to pain or discomfort or visual changes or other functional changes for the organ, tissue, or organism, changes that lead to tear film irregularities, changes that lead to fluorescein dye uptake or other vital dyes that are used in epithelial cell assessments (lissamine green, Rose Bengal), damage to the eye, and alterations affecting normal cell heath. Adverse events include but are not limited to medical problems, cellular health problems, tissue health problems, organ health problems, or organism health problems that happen(s) during treatment with a drug, pharmaceutical or other therapy. Drug and pharmaceutical may be used interchangeably herein.

For purposes herein, passivation moieties may be and typically are considered hydrophilic moieties, however, alternative moieties may passivate with properties where hydrophilicity does not dominate.

In another embodiment of the invention disclosed herein, an antibody is designed and directed at an ADC with associated corneal toxicity, where the antibody further comprises a passivation moiety, and is delivered to the eye in an amount effective to reduce ocular adverse events such that the antibody with a passivation moiety specifically and directly interacts with a molecular component of the ADC interfering with the activity and/or binding of the ADC with off-target cells, including corneal cells.

Another embodiment of this invention is a method to nonspecifically inhibit corneal toxicity resulting from adverse drug effects where the inhibition is mediated by nonspecific interactions (electrostatic or hydrophobic) of a copolymer described herein, including a graft or block copolymer with either cationic, hydrophobic, or anionic moieties and a hydrophilic passivation moiety, with a cytotoxic agent, and thereby reducing through the effect of passivation moieties the adverse effects of drugs with deleterious effects on the cornea. In some embodiments, the drug with adverse corneal events is an ADC; in other embodiments the drug or pharmaceutical is a small molecule. The pharmaceutical may be a biological, an antibody, and antibody-drug conjugate, a large molecule or a small molecule. A small-molecule drug is any organic compound that affects a biologic process with a relatively low molecular weight, below 900 Daltons. A large-molecule drug is any organic compound that affects a biologic process with a relatively low molecular weight, above 900 Daltons. A large molecule may be an organic compound, a pegylated compound, a protein, a biologic, or a peptide. Peptides may be small or large molecules depending on the molecule weight of the molecule. A biologic or biologic drug in the setting of a pharmaceutical herein is a product that is produced from living organisms or contains components of living organisms.

In some embodiments the drug is selected from the group of: Cationic amphiphilic drugs, amiodarone, aminoquilones, Chloroquine, hydroxychloroquine(Plaquenil), amodiaquine, mepacrine, Tafenoquine, thorazine, tamoxifen, NSAID s, ibuprofen, indomethacin, naproxen, benoquine, atovaquone, suramin, tilorone, perhexiline maleate, gentamicin, tobramycin, clarithromycin, ciprofloxacin, clofazimine, gold salts, vandetanib, osimertinib, small molecules may be selected from kinase inhibitors, erlotinib, and cytarabine, but not limiting. Corneal vortex keratopathy, corneal deposits, epitheliopathies, verticillata, corneal lines, Hudson Stahl lines, crystal like deposits, stromal inflammation, and corneal opacifications may be reduced or prevented. Limbal stem cell deficiency may be prevented for pharmaceutical agents associated with that limbal stem cell dysfunction toxicity. Pannus, corneal neovascularization, conjunctival epithelialization of the cornea may be reduced or prevented. Without being bound to any particular method, the copolymer passivates the cytotoxic agent found in tears and/or reaching limbal stem cells from the perilimbal circulation.

In another aspect, a method to decease the adverse events associated with any drug's corneal toxicity by treating cells at risk with the copolymer or a solution bathing those cells.

In another aspect, a method to decrease adverse events associated with antibody-drug conjugate usage in the setting of an off-target uptake pathway (or without such an off-target pathway where the toxicity is more direct—either through target uptake, cell receptor similarities to ADC binding sites, or warhead entrance into at risk cells) that is causing damage to nonneoplastic cells, by applying an effective amount of a copolymer to a solution bathing such cells.

The fundamental methodology of decreasing adverse events in cells including corneal cells, associated with their exposure to an antibody-drug conjugate is exposure via solution or suspension, prolonged or acute, of (or to) cationic graft copolymers to the eye and/or corneal cells including precursor epithelial cells, transient amplifying cells, basal epithelial cells, and differentiated epithelial cells, and stem cells (and daughter cells) via topical, local, or systemic approaches (in certain cases) to limit uptake, including macropinocytotic uptake of the ADC. PLL-g-PEG is particularly safe and effective in this setting. Other similar approaches are considered.

Copolymers of the current invention have a bioadhesive moiety as described above (cationic, anionic, hydrophobic) and a passivating moiety (hydrophilic, sometimes chemically inert, where "chemically inert" means without an ability to covalently or electrostatically or using hydrophobicity to significantly react with cells or proteins) such that interaction of viruses and ADC's with the cell compromised by infection or toxicity, respectively, is reduced. All moieties can have varying MW sizes, and combination polymers can be utilized. Formulations with multiple copolymer structures can be utilized. Polydispersity among polymers is known and anticipated in manufacturing and does not reduce effectiveness.

U.S. Pat. Nos. 9,884,074; 9,295,693; 9,283,248; 9,005,596; 8,802,075 discuss graft copolymers and uses for these multifunctional copolymers and are incorporated herein by reference. US patent 2004/0181172 A1 was reviewed; it discusses tear collection for analyzing tears.

Method steps of the invention include to apply the copolymers with bioadhesive and passivation moieties to at risk cells and tissue.

A preferred mode of the invention is through the application of PLL-g-PEG to at risk cells and tissues, preferably before exposure, although its use after exposure confers benefits in reducing severity of adverse findings (secondary epithelial cell damage or repeated exposures or infection or reinfection may be reduced) and reducing the extent of adverse events (minimizing continued uptake by the ADC).

Without being bound to a particular mechanism for ADC's, on-target toxicity, it includes an antibody/receptor mediated uptake into an epithelial cell that may lead to adverse events can be also be reduced in this mode (in a local environment particularly). Embodiments of this invention address this approach to ameliorating or mitigating ADC toxicity as well. For example, a copolymer passivates an ADC locally to reduce on-target toxicity if a corneal epithelial cell expresses a receptor or protein target on the cell surface that initiates cell uptake.

In one embodiment of this invention, a co-polymer eye drop containing formulation may be provided as a kit with a supply of one or more months of eye drop delivery systems possibly along with a chemotherapeutic agent at time of initiation, or consideration for ADC therapy. Kits and eye drops may be delivered to the patient by mail or similar delivery services and may be refilled online.

In some embodiments, the copolymer is supplied as a pharmaceutical composition in eye drop bottles, multi-dose preservative free bottles, standard three-piece bottles, unit dosers/blow fill and seal containers. Eye drop bottle fill volumes are between 1 ml and 30 ml typically. Blow fill and seal containers of various sizes with fills from 0.1 mL to 1 mL (0.5 mL fill, 0.3 mL fill, 0.4 mL fill, 0.7 mL fill) are examples for unit-doser fills. Aerosols, sprays, misters, mechanized or electronic spray bottles, pump spray bottles, liquids for mouthwashes, liquids for consumption, powders, concentrated solutions for dilution, and other commercially available systems to provide consumer goods with pharmaceutical ingredients. A kit can be sold with an eye drop, nasal spray, and mouth rinse. A kit can include a supply of eye drops with an ADC for oncologic or other disease care.

Advantages include that there are currently no methods to reduce the risk of infection by application of a protective material to the mucous membranes, and that is needed in the arsenal against viral disease.

Advantages include that besides supportive care such as warm compresses, bandage contact lenses, and ocular lubricants, there are no therapies that reduce the risk of ADC corneal toxicity based on reducing ADC/epithelial cell interaction.

DETAILED DESCRIPTION OF THE INVENTION

Figure 1:
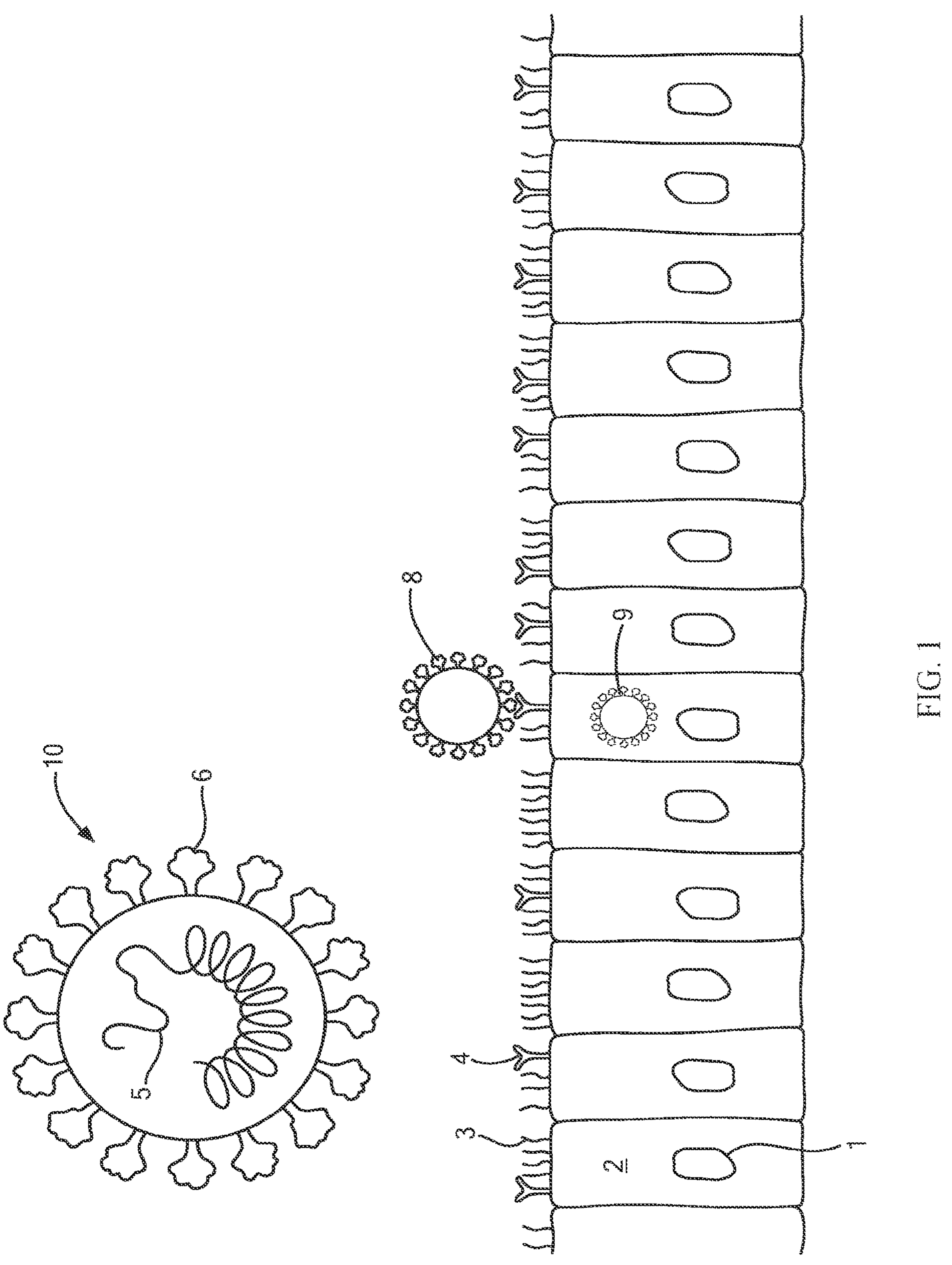
FIG. 1 as expected shows a SARS-CoV-2 viral particle in the presence of respiratory epithelial cells. 1. Respiratory epithelial cell nucleus. 2. Respiratory epithelial cell. 3. Cell villi. 4. ACE2 receptor. 5. SARS-CoV-2 viral particle RNA. 6. SARS-CoV-2 viral particle spike protein. 8. The virus binds to the ACE2 receptor. 9. The virus enters the cell. 10. The SARS-CoV-2 virus.
Figure 2:
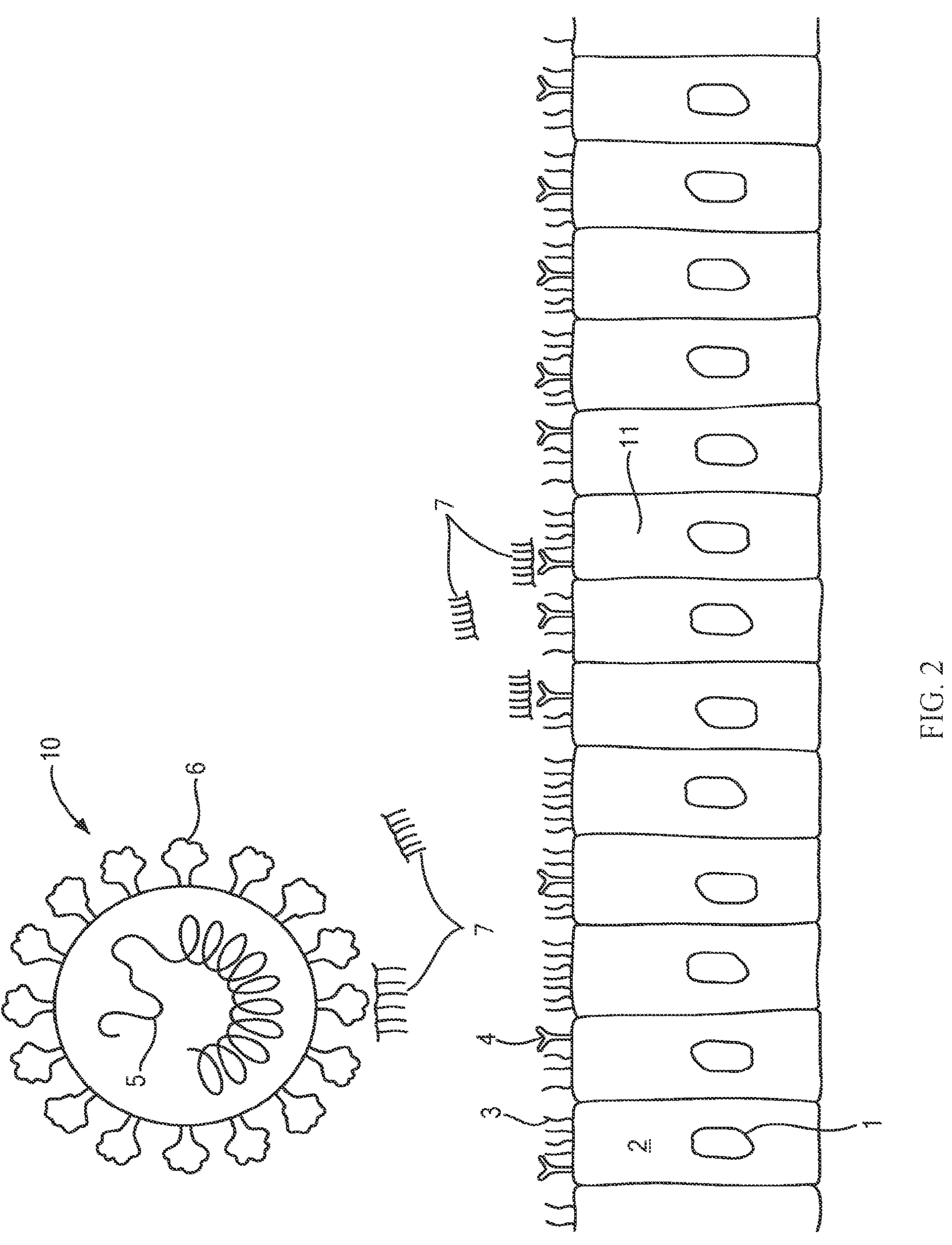
FIG. 2 as expected shows a SARS-CoV-2 viral particle in the presence of respiratory epithelial cells and a cationic graft copolymer and the interference imparted by the co-polymer blocking ACE2 related viral cell entry. Although Figure depicts a respiratory epithelial cell, other epithelial cells that may be infected with SARS-CoV-2 may be substituted. 1. Respiratory epithelial cell nucleus. 2. Respiratory epithelial cell. 3. Cell villi. 4. ACE2 receptor. 5. A SARS-CoV-2 viral particle RNA. 6. SARS-CoV-2 viral particle spike protein. 7. Cationic graft copolymer. 11. The virus does not enter the cell because of the interfering effect of the cationic graft copolymer (which is PLL-g-PEG in some embodiments).
Figure 3:
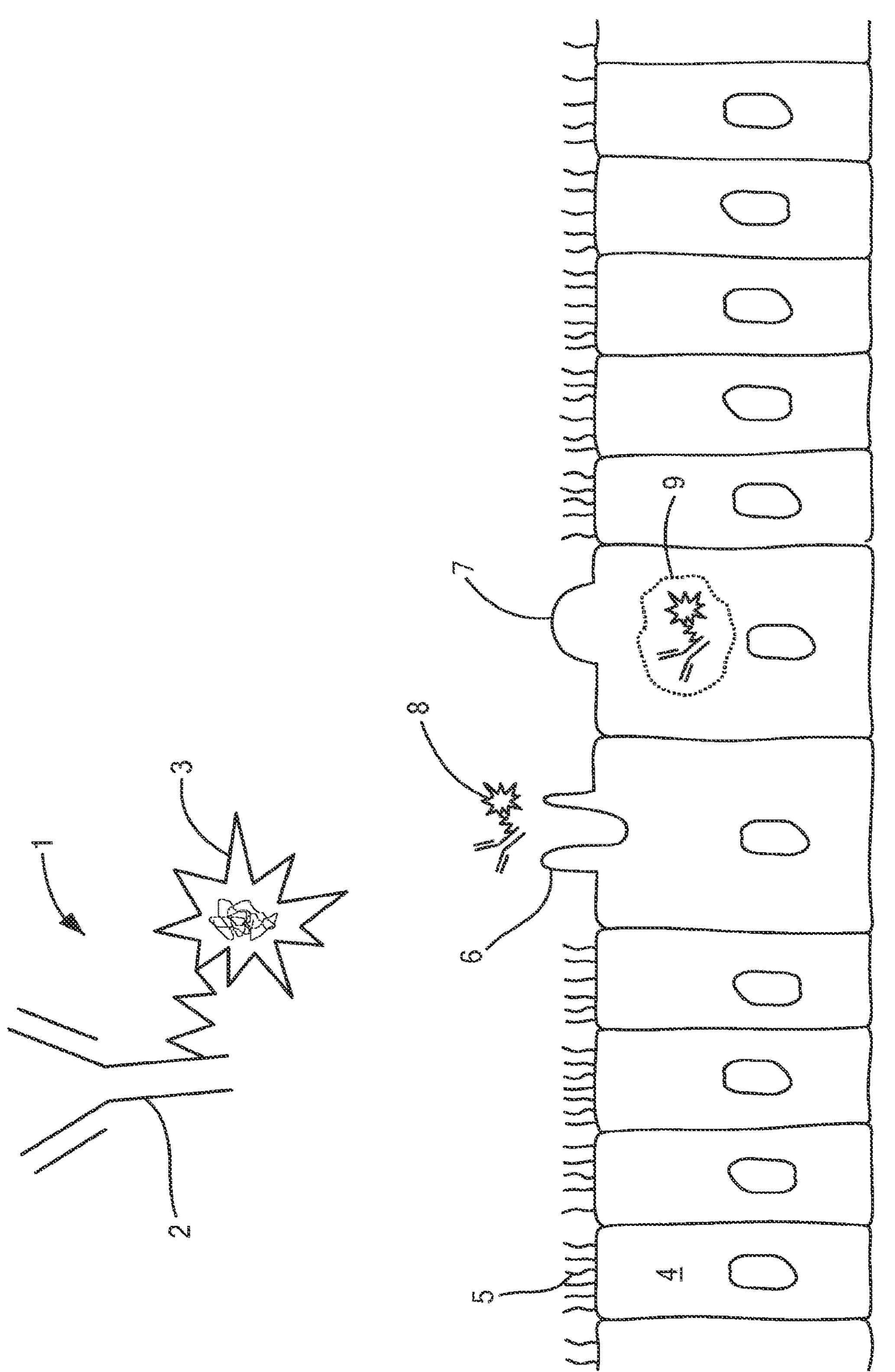
FIG. 3 as expected shows an antibody drug conjugate in the presence of corneal epithelial cells. 1. ADC 2. Antibody component. 3. Toxic payload. 4. Corneal epithelial cell. 5. Corneal epithelial cell microvilli. 6. Initiation of macropinocytosis. 7. Completion of macropinocytosis. 8. ADC engaging with macropinocytotic process where ADC is about to be captured by corneal epithelial cell from the extracellular fluid. 9. ADC with toxic payload inside epithelial cell and in lysosome, where the payload will be cleaved from the ADC and released into the cell where it will damage or kill the cell.
Figure 4:
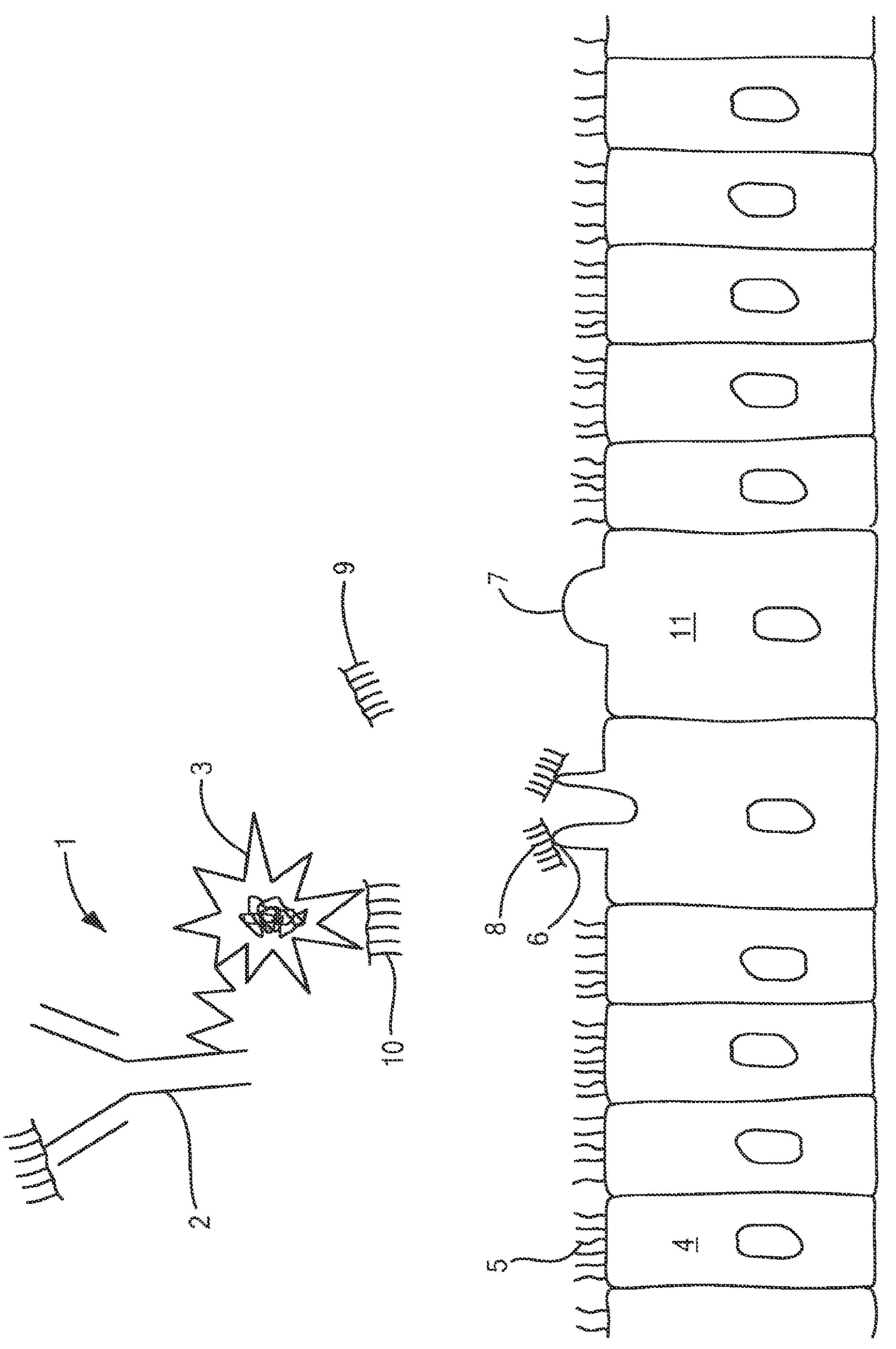
FIG. 4 as expected shows an antibody drug conjugate in the presence of corneal epithelial cells and a cationic graft copolymer (which is PLL-g-PEG in one embodiment), note the corneal epithelial cell may be a transient amplifying cell, wing cell, basal epithelial cell, or limbal epithelial stem cell. Drawing, for simplicity, depicts a surface epithelial cell. 1. ADC 2. Antibody component. 3. Toxic payload. 4. Corneal epithelial cell. 5. Corneal epithelial cell microvilli. 6. Initiation of macropinocytosis. 7. Completion of macropinocytosis. 8. PLL-g-PEG on corneal epithelial cell surface. 9. PLL-g-PEG in solution. 10. PLL-g-PEG adhering to ADC at several locations. 11. Lack of ADC with toxic payload inside epithelial cell. Cell injury and death is prevented.
Figure 5:
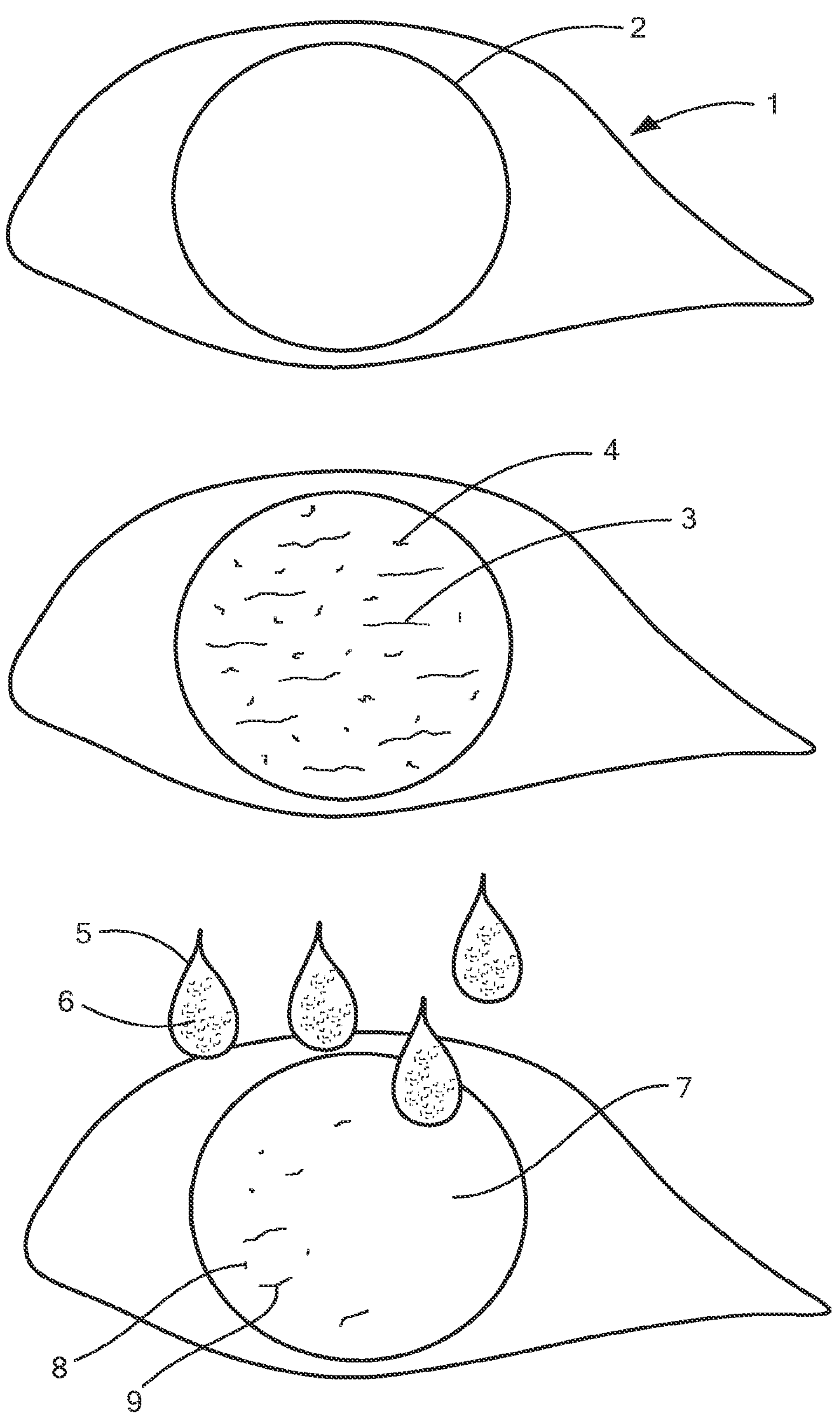
FIG. 5 as expected shows the benefit of cationic graft co-polymer eye drop treatment on an eye in the presence of systemically administered ADC. 1. A schematic of the front of the eye. 2. Schematic of the cornea. 3. Superficial punctate keratitis on the surface of the cornea. 4. Microcyst-like changes in the corneal epithelium noted after a patient has been treated with systemic ADC for cancer. 5. Eye drop containing PLL-g-PEG being administered to the eye of a patient receiving systemically administered ADC for cancer. 6. PLL-g-PEG in solution in the eye drop. 7. Cornea with much healthier appearing surface in ADC treated patient and PLL-g-PEG eye drop treated patient. 8. Fewer microcyst-like changes in PLL-g-PEG eye drop treated patient. 9. Less superficial punctate keratitis in PLL-g-PEG eye drop treated patient, despite ADC on board systemically.

It has now been found that a graft co-polymer having a positively charged moiety and a hydrophilic moiety or a block co-polymer having a positively charged or moiety and a hydrophilic moiety are effective in two important aspects of human health.

First, these polymers are effective at reducing viral infectivity and infection severity if infection occurs by contact with epithelial surfaces, as well as other exposure methods. It is known that viral dose may relate to the severity of an infection on a dose-response type basis. Even if an infection does occur, reducing the number of viral infections in cells will have beneficial effects on disease course (an intervention that is 100% effective is rare).

Second, these polymers are effective at reducing antibody-drug conjugate (ADC) toxicity on nonneoplastic cells. These polymers are able to interfere with off-target cell uptake of ADC's with cytotoxic payloads into cells that do not express the ADC's target receptor. Through topical exposure, they also can reduce uptake by locally treating tissue to passivate the ADC. (Copolymer may be in the lining mucosal solution or extracellular space to interfere with off target ADC uptake.) Specifically, regarding off target uptake these cationic graft or cationic block copolymers interfere with macropinocytosis of an ADC by a human corneal epithelial cell, including a basal epithelial cell, limbal stem cell, basal stem cell, wing cell, or superficial epithelial cell. This reduction of exposure of the internal cell body, or cytoplasm, including lysosomes, and in some embodiments to tubulin forming components provides a benefit to the cell and organism.

Without being bound to theory, the method of interference is that the graft or block copolymers passivate the surface of the cell to be affected and/or the ADC or virus such that cell uptake is prevented or reduced. The cationic graft copolymer or other polymeric embodiments interact with a biological surface and/or the surface of a virus or an ADC.

The key discovery is the ability of a cationic graft copolymer such as PLL-g-PEG to be effective in this setting. It is safe and well tolerated, and highly efficacious. There are multiple embodiments of PLL-g-PEG that are effective, and these polymers are tunable.

Definitions

By "off target uptake" is meant the entry of an ADC into a cell using a mechanism different or not completely dependent on the antibody—cell receptor interaction for which the targeted therapy was designed.

"New viruses" can mean new to a host (human or otherwise), or not encountered in humans before.

A host is the living being that the bacteria, virus, protozoan, or other disease-causing microorganism normally resides in.

"Biological Surface" means surface of a cell, tissue, bodily organ, whether it be exposed to the external environment, or internal to the body. For example, the surface of the eye includes the epithelial cell covered cornea and conjunctiva, as well as the posterior tenons layer and sclera; the epithelial layers of the gastrointestinal tract or the skin are included, membranes such as mucous membranes, including oral, nasal, respiratory, and vagina mucous membranes. Other surfaces include the capsules of organs such as the spleen and liver, and the outermost aspect of bone, cartilage, and muscle. Copolymers described herein may also interact at the surface of the virus and ADC to confer benefit.

"Formulation" means a solution, suspension, powder, spray, rinse, eye drop, administered to a cell, tissue, organ, or mammal to be treated that includes the necessary components to enable the beneficial effect from the graft or block copolymer to take place. A formulation may or may not include an active pharmaceutical ingredient. For the purposes of this invention, the graft copolymer may or may not be considered an active pharmaceutical ingredient by regulatory authority terminology. The eye drop formulations may have various percentages of the copolymers (an effective range), may have a pH between 3.9 and 9.9, may have an osmolality between 150 and 400, may have a viscosity between 1.0 and 15 cP. Viscosities can go much higher in some embodiments. Formulations are safe for subconjunctival injection.

"Microtubule disruption" is considered a cytotoxic effect of particular interest herein. Examples of these "cytotoxic agents" include but are not limited to MMAF (Monomethyl auristatin F (MMAF) is an antitubulin agent agent that inhibits cell division by blocking the polymerization of tubulin), MMAE (monomethyl auristatin E), DMF (dimethylformamide), Maytansine, aurastatins, DM4 (Ravtansine) and DM1 (Mertansine). Other cytotoxic agents are listed elsewhere, some in combination with antibodies. All are included, and unknown cytotoxic agents as well, are included in various embodiments.

The "cytotoxic payload" may also be called a "warhead". Linkers are used to join the antibody with the warhead. Linkers are cleaved by intracellular and sometimes extracellular enzymes. In particular, linkers are cleaved in lysosomes releasing the warhead within the cell. Extracellular fluid or enzymes in tears may in some instances cleave a linker a release a warhead. Warheads may thus directly enter cells or, warheads may leak out of cells and cause a bystander effect (damage cells nearby that did not uptake the ADC). Any linkers, and there are many (both known and unknown) are considered in embodiments of this invention. Linkers nay be specific to cells and treatment situations.

As used herein, the term "pharmaceutical composition" refers to a composition in which an active agent is formulated together with one or more pharmaceutically acceptable carriers. The composition is suitable for administration to a human or animal subject. The active agent is present in unit dose amount appropriate for administration in a therapeutic regimen that shows a statistically significant probability of achieving a predetermined therapeutic effect when administered to a relevant population.

Formulations of copolymers in the present invention include embodiments using many types of formulations including gels, lotions, creams, ointments, sprays, wipes, salves. Formulations may be preserved or unpreserved. Formulations may be monophasic or multiphasic. Without limitations, phasic formulations have varying amounts of different components to affect efficacy and duration of activity. Some formulations have prolonged activity, others have shorter activity. In general, a single application provides at some meaningful duration of time protection. A "meaningful duration of time" for the purposes herein means up to 0.1 minute, up to 0.5 minute, up to 1 minute, up to 15 minutes, up to 30 minutes, up to one hour, up to two hours, up to three hours, up to four hours, or up to six to twelve hours typically. In some embodiments, duration is longer than 12 hours. Extended-release formulations will increase the duration of action. The duration of activity value can be shorter or longer regarding viral protection and ADC toxicity reductions, as determined in development. For methods of ADC toxicity attenuation and mitigation, dosing may range from daily to hourly depending on the formulation and/or payload of the ADC, patient status, and underlying condition, and formulation. The use of these approaches in vitro (as well as in vivo) has practical value and may be shorter or longer depending on the in vitro model.

Animal data for other uses with small interfering RNA molecules has shown PLL-g-PEG can be tolerated intravenously. PLL-g-PEG is well tolerated locally and has thus particular value herein. By "tunable" it is meant that a cationic graft copolymer can be prepared, and remain useful, in various ways. For example, the length of the PLL chain, the graft ratio to mer in the polymer, and the length of the hydrophilic side chain are tunable. By way of example, the PLL-g-PEG molecules utilized in the experimental proof, or reduction to practice for this invention include, PLL (15,000 to 30,000 Daltons)—graft (3.5 ratio)—PEG (5,000). Alternative molecule weights and graft ratios can be equally, more so, or slightly less effective. For the purposes of this invention, all PLL-g-PEG variations are effective and are referred to as PLL-g-PEG. Mimetics can be similarly tunable. Because PEG is a hydrophilic molecule, it has been used to passivate microscope glass slides. Polyethylene glycol has a low toxicity and is used in a variety of products. The polymer is used as a lubricating coating for various surfaces in aqueous and non-aqueous environments.

Regarding specifics of the PLL-g-PEG. Polylysine (PLL) facilitates the attachment of proteins and cells to surfaces. The PLL may be larger than 30,000 Daltons even up to 60,000 Daltons or higher or it may be smaller than 15,000 Daltons. Ranges of polydispersity are acceptable. A polydispersity index of 0.3, 0.5, 0.8, 1 or 1.2 is considered acceptable (inclusive), as is any range from 0.1 to greater than 3. Sometimes, PLL can be reported as a single size (e.g. 20,000 Daltons). Larger or smaller PLL molecules are effective in this setting. The preferred configuration is a mean PLL size between 10,000 and 40,000, but larger or smaller PLL sizes are effective. Polydispersity indexes can vary and still be effective. The number of lysine (L lysine, D Lysine, alpha, or epsilon polylysine but not limited to) mers can be 50 to 200 in some embodiments, longer or shorter (fewer or more mers) are OK. The grafting ratio is optimally 3.5 or 4 PLL:PEG, however a reasonable preferred range is 2 to 6. Above 6 to 7, 8, 9, or 10 is acceptable in some embodiments. The upper limit is simply the point at which tolerability is reduced. It is anticipated efficacy will decrease as the graft ration falls below 2, however, 1.1 is probably the lower limit of optimal benefit from the mechanism with the cationic PLL chain utilizing charge for bioadherence. Hydrophobic chains and other configurations may have different success rates and are also tunable. The hydrophilic moiety, in this case PEG can also have different sizes or lengths. PEG 5,000 Daltons is one preferred embodiment, but PEG 2,000 is also effective. Ranges of PEG molecular weights that in this specific molecule's use are effective include PEG 1000 to PEG 20,000. Ranges and variable polydispersities are acceptable (0.1 to over 2). The ethylene glycol mers can be counted as well, as an alternative to a molecular weight reported in Daltons. A reasonable range is 22 to 250 mers here. In some embodiments, the mer count is between 50 to 150. In some embodiments it is over 250. These factors are tunable, and the same or similar effectiveness can be seen with carrying PLL size, graft ratio, and PEG size. Optimal, but not limiting, configurations are described. Mixtures of different base PLL-g-PEG copolymers are acceptable. Multiple different linkers of mPEG to PLL are acceptable. Mimetics, as outlined herein can be addressed similarly with graft ratio, backbone size, and hydrophilic/passivation moiety size.

Accordingly, the present invention provides methods for inhibiting, reducing, or preventing viral (e.g. SARS-CoV-2) infectivity and reducing the severity of the disease course can be accomplished in a subject via topical or local administration of a formulation comprising a graft co-polymer having a positively charged moiety and a hydrophilic moiety or a block co-polymer having a positively charged moiety and a hydrophilic moiety to a biological surface of a subject. Because charge dynamics are complex, negative charge-based passivation methodology can also be identified, and these discoveries are also considered and utilized herein. Formulations with the polymers claimed herein can be administered topically or locally in accordance with methods of the present invention to biological surfaces of a subject including, but not limited to, skin, mucous membranes, oral mucosa, nasal mucosa, and the surface of the eye. By "subject", as used herein it is meant to be inclusive of all animals and in particular mammals such as, but not limited to, humans and dogs as well as agricultural animals such as bovine, ovine, and porcine.

Graft co-polymers used in the methods and formulations of the present invention are polymers having a linear section of repeat units called the "backbone", with at least one side chain of repeat units (called a "graft"), usually of a different chemistry, branching from a point along the backbone. In one embodiment, the graft co-polymer comprises a cationic backbone and side chains that are water soluble and non-ionic. In another embodiment, the graft copolymer comprises a water-soluble non-ionic backbone and cationic side chains. In another embodiment, negative or anionic graft copolymers are utilized.

Block co-polymers used in the methods and formulations of the present invention are polymers in which linear sections of a first section of repeat units are connected end-to-end with linear sections of subsequent repeat units that are chemically dissimilar to the first.

Formulations for use in the methods of the present invention comprise a block or graft co-polymer having one section, either the backbone, the graft or the block, that adheres to a biological surface tissue such as, but not limited to, cells, epithelial cells, mucosa, mammalian tissue, respiratory cells, alveoli, tracheal and bronchial tissue, nasal mucosa, oral mucosa, and the eye surface including corneal and conjunctival epithelial cells as well as limbal stem cells, limbal cells, limbal epithelial stem cell, basal stem cells, basal cells, early transient amplifying cells, transient amplifying cells, and corneal epithelial cells generally, as well as the glycocalyx and microvilli associated with any such cells. In addition to electrostatic forces bioadhesion, another, chemically different section, either the backbone, the graft, or block, is hydrophilic and induces a passivation and reduction of interaction between viruses in one embodiment and ADCs in another. Interactions are effectively diminished for benefits to human health. Viral transmission and contagious diseases transmissions can be reduced, especially those for which there is insufficient host or herd immunity to prevent an epidemic or pandemic. One embodiment is a method for decreasing novel viral infectivity for which humans have not developed herd immunity to help mitigate disease and the severity of epidemics and pandemics.

A patient is a human but can also be a mammal.

Human health is improved by reducing ADC toxicity in general, and to the eye and cornea specifically. Specifically, the health of the corneal epithelium is promoted. Patients can better tolerate ADC's for the treatment of malignancy or other conditions while maintaining healthier corneal epithelium resulting in fewer and less severe reductions in eyesight/visual acuity and fewer and less symptomatic eyes. The tissue-adhesive sections of a graft or block co-polymer in the formulations used in the methods of the present invention may be cationic, in which case the polymer adheres to the biological surface by electrostatic attraction. The interaction may be anionic or hydrophobic using hydrophobic moieties in combinations herein as well-hydrophobic interactions, as well as anionic interactions hold promise.

Examples of cationic polymer sections of graft or block co-polymers of formulations useful in the methods of the present invention include, but are not limited to: poly(L-lysine) (PLL), poly(2-vinyl pyridine) and poly(4-vinyl pyridine) and vinyl co-polymers containing those repeat units, and poly(aminoethyl methacrylate) homo- and co-polymers containing N,N dimethylaminoethylmethacrylate) repeat units. Another cationic polymer section which can be used is chitosan (a co-polymer of glucosamine and N-acetyl glucosamine where 5-100% of the repeat units are glucosamine) and synthetic derivatives thereof. Examples of hydrophobic polymer sections of graft or block co-polymers of formulations useful in the methods of the present invention include, but are not limited to, long-chain aliphatic hydrocarbons, polyethylene, poly(propylene oxide), polystyrene, poly(methylmethacrylate), poly(butylenes oxide), and the like. The hydrophilic section of the polymer may be non-ionic if the tissue adhering section is cationic, or anionic if the tissue-adhering section is non-ionic (and hydrophobic).

Examples of anionic polymer sections of graft or block co-polymers of formulations useful in the methods of the present invention include, but are not limited to: polyacrylic acid (PAA), polymethacrylic acid, poly(sodium styrene sulfonate), carboxylated cellulosics such as carboxymethylcellulose (CMC), poly(itaconic acid), poly(maleic acid), poly(aspartic acid), poly(glutamic acid), polyphosphates, polynucleic acids, poly(acrylamidopropanesulfonic acid), anionic natural gums, anionic carbohydrates, carageenan, alginates and hyaluronic acid.

Examples of non-ionic hydrophilic polymer sections of formulations useful in methods of the present invention include, but are not limited to, poly(ethyleneglycol) (PEG), poly(vinylalcohol), poly(vinylpyrrolidinone), and the like. Examples of anionic hydrophilic polymer sections include homopolymers and co-polymers containing, for example, acrylic acid, methacrylic acid, itaconic acid, maleic acid, styrene sulfonic acid, carboxymethyl cellulose, carboxyethylcellulose, succinylated chitosan, cellulose sulfate, and the like.

By block or graft co-polymers it is meant to describe the architecture of the polymer.

By "mimetic polymers" it is meant an alternative chemical/molecular approach to creating the same behavior and attributes of an effective and tested polymer. Multiple mimetics exist as, for example, PLL-g-PEG is effective. The effect is primarily drawn from the macromolecular passivation.

By "passivation" it is meant that a cell or biological surface has a reduced interaction capability with a virus or antibody drug conjugate such that infection or macropinocytosis, cell internalization of the virus or ADC, is reduced. The phenomenon is also steric interference and also reduces an ability of charge interactions to play a role in the virus or ADC interaction. By "passivation" it is also meant that a virus or ADC surface has a reduced interaction capability with a cell at risk such that infection or macropinocytosis, cell internalization of the virus or ADC, is reduced.

Passivation may occur on the ADC, cytotoxic drug, or virus. Passivation may also take place by interactions on the cells to make them less susceptible to ADC, drug, or virus uptake.

Graft co-polymers may have a cationic (or non-ionic hydrophobic or anionic) backbone made from a polymer chosen from the list, supra, and hydrophilic grafts, or have a hydrophilic backbone, and cationic (or non-ionic hydrophobic) grafts chosen from the list, supra. For graft co-polymers, grafts may arise from every repeat unit in the backbone or may be intermittently spaced along the backbone (with uniform or random frequency). For example, a useful polymer in formulations for use in the methods of the present invention is PLL-g-PEG where the backbone is the cationic polymer poly(L-lysine) and the grafts are made from the hydrophilic polymer poly(ethylene glycol). The PLL backbone may be from 3 repeat units to several thousand repeat units long, and the PEG grafts may be from 1 to several thousand repeat units long. The PEG grafts may be attached to every PLL repeat unit, every other PLL repeat unit, every third repeat unit or less frequent. In one embodiment, there is a PEG graft on average at every third PLL repeat unit. Similar characteristics may be applied to mimetic polymers.

Block co-polymers comprising at least one block that is cationic and at least one block that is water soluble and non-ionic are also useful in formulations for use in methods of the present invention. In one embodiment, the block co-polymer comprises at least one block which is hydrophobic and at least one block which is water soluble and anionic, cationic or non-ionic. Anionic blocks are considered.

Examples of water soluble non-ionic co-polymer blocks include, but are not limited to, poly(ethylene glycol) (PEG), polyvinyl alcohol (PVA), poly(hydroxyethyl methacrylate) (pHEMA), poly(acrylamide), poly (vinyl pyrrolidone) (PVP), poly(ethyl oxazoline) (PEOX), polysaccharides, and copolymers of any two or more thereof.

Examples of water soluble anionic co-polymer blocks or backbones include, but are not limited to, polyacrylic acid (PAA), polymethacrylic acid, poly(sodium styrene sulfonate), carboxylated cellulosics such as carboxymethylcellulose (CMC), poly(itaconic acid), poly(maleic acid), poly(acrylamidopropanesulfonic acid), anionic natural gums, anionic carbohydrates, carageenan, alginates and hyaluronic acid.

Examples of water soluble cationic co-polymer blocks include, but are not limited to, polymers based on vinyl pyridine, N,N-dimethylaminoethylacrylate, N,N-dimethylaminoethylmethacrylate, allyl tri(alkyl) ammonium halides, poly(amino styrene), chitosan, polyethyleneimine, polyallylamine, polyetheramine, polyvinylpyridine, polysaccharides having a positively charged functionality thereon, polyamino acids such as, but not limited to, poly-L-histidine, poly-im-benzyl-L-histidine, poly-D-lysine, poly-DL-lysine, poly-L-lysine, poly-ε-CBZ-D-lysine, poly-ε-CBZ-DL-lysine, poly-ε-CBZ-L-lysine, poly-DL-ornithine, poly-L-ornithine, poly-Δ-CBZ-DL-ornithine, poly-L-arginine, poly-DL-alanine-poly-L-lysine, poly(-L-histidine, L-glutamic acid)-poly-DL-alanine-poly-L-lysine, poly(L-phenylalanine, L-glutamic acid)-poly-DL-alanine-poly-L-lysine, and poly(L-tyrosine, L-glutamic acid)-poly-DL-alanine-poly-L-lysine, copolymers of L-arginine with tryptophan, tyrosine, or serine, copolymers of D-glutamic acid with D-lysine, copolymers of L-glutamic acid with lysine, ornithine, or mixtures of lysine and ornithine, and poly (L-glutamic acid).

Examples of hydrophobic co-polymer blocks include, but are not limited to, alkanes, alkenes, alkynes, poly(isobutylene), polyesters such as poly(caprolactone) (PCL), poly (lactic acid) (PLA), poly(glycolic acid) (PGA), and copolymers therefrom (PLGA), polyamides such as nylon(6,6) and Nylon(12), polyurethanes, poly(propylene oxide), poly(tetramethylene oxide), polyethylene, polypropylene, polystyrene, poly(acrylates) such as polymethyl acrylate (PMA), poly(methacrylates) such as poly(methylmethacrylate) (PMMA), poly(sulfones), poly(etheretherketones) (PEEKs), poly(phosphazines), poly(carbonates), poly(acetals) and poly(siloxanes).

If in the descriptions above and herein, one molecular entity can apply to another paragraph, but was omitted, it can be considered where applicable so included. Similarly, terms can be moved about where indicated to support eventual claims.

As will be understood by the skilled artisan upon reading this disclosure, graft and block as well as triblock and dendrimers are contemplated, and these configurations can also be used as embodiments of the current invention.

An exemplary block co-polymer comprising a triblock configuration is PLURONIC® F127, also referred to as Poloxamer 407, containing a poly(ethylene oxide) hydrophilic block ("PEO"), a poly(propylene oxide) hydrophobic block ("PPO") and another PEO block. Other block co-polymers for use in the present invention may contain only one hydrophilic block and one hydrophobic block, or may contain several alternating blocks, for example the PPO-PEO-PPO block co-polymers (PLURONIC®, block co-polymers based on ethylene oxide and propylene oxide, BASF, Florham Park, NJ). Additional exemplary PLURONIC block co-polymers useful in the present invention include, but are not limited to, PLURONIC 10R5, PLURONIC 17R2, PLURONIC 17R4, PLURONIC 25R2, PLURONIC 25R4, PLURONIC 31R1, PLURONIC F 108 Cast Solid Surfacta, PLURONIC F 108 Pastille, PLURONIC F 108 Prill, PLURONIC F 108NF Prill Polaxamer 338, PLURONIC F 127 Prill, PLURONIC F 127 NF, PLURONIC F 127 NF 500 BHT Prill, PLURONIC F 127 NF Prill Poloxamer 407, PLURONIC F 38, PLURONIC F 38 Pastille, PLURONIC F 68, PLURONIC F 68 Pastille, PLURONIC F 68 LF Pastille, PLURONIC F 68 NF Prill Poloxamer 188, PLURONIC F 68 Prill, PLURONIC F 77, PLURONIC F 77 Micropastille, PLURONIC F 87, PLURONIC F 87 NF Prill Poloxamer 237, PLURONIC F 87 Prill, PLURONIC F 88 Pastille, PLURONIC F 88 Prill, PLURONIC F 98, PLURONIC F 98 Prill, PLURONIC L 10, PLURONIC L 101, PLURONIC L 121, PLURONIC L 31, PLURONIC L 35, PLURONIC L 43, PLURONIC L 44, PLURONIC L 44 NF Polaxamer 124, PLURONIC L 61, PLURONIC L 62, PLURONIC L 62 LF, PLURONIC L 62D, PLURONIC L 64, PLURONIC L 81, PLURONIC L 92, PLURONIC L44 NF INH surfactant Polaxamer 124, PLURONIC N 3, PLURONIC P 103, PLURONIC P 104, PLURONIC P 105, PLURONIC P 123 Surfactant, PLURONIC P 65, PLURONIC P 84, and PLURONIC P85.Where applicable, all particle sizes of the block copolymers are included, for example PLURONIC F127 and PLURONIC F87 are available as prill and microprill products. Non-ionic surfactants, for example, containing a hydrophobic segment and a PEO block are considered here as block co-polymers.

Additional exemplary block or graft co-polymers which can be used in the present invention are disclosed in U.S. Pat. Nos. 5,578,442 and 5,834,556, teachings of each are herein incorporated by reference in their entirety.

The block or graft co-polymers are included in formulations for use in the methods of the present invention at concentrations ranging between 0.001% and 40%, more typically 0.01% to 25%, on a weight/weight basis as a component of the formulation. The formulation is, in some embodiments, a powder, such as a lyophilized powder for delivery to tissue or for reformulation and dissolution, the powder may be from 0.001% to 100% block or graft copolymer. Copolymers may be water soluble in some embodiments. Combinations of the copolymers are considered and included herein whereas the percentage of the formulation may apply to each different component.

In the Examples in humans in which the formulation is described at present, when delivered as solutions or suspensions, the amounts of co-polymers are between about 0.1% and 5%. In addition, the amount of co-polymer can be, 0.01% to 3%, 0.1% to 2.5%, or 0.5 to 4%.

Additional exemplary components which can also be incorporated into pharmaceutical formulations and coatings for use in the present invention include, but are not limited to, PLURONIC gelling agents such as, but not limited to F127, F108 as well as additional PLURONIC agents listed supra. Furthermore, in one embodiment, these components are used at fractions below that required for gelling activity.

Other components (either active or inactive ingredients) which can be included in these pharmaceutical formulations include, but are not limited to, lipids, oils, surfactants, water, lubricating polymers, typical surfactants, buffers, salts, physiologic ions, proteins, topical emollients, excipients typically used in oral, topical, mucosal, dermatologic and ophthalmic formulations, lubricants such as PEG 400, carboxymethylcellose, hydroxypropyl methylcellulose, mineral oil, propylene glycol, glycerin, hypromellose, white petrolatum, polyvinyl alcohol, liposomes, mannitol, hydroxypropyl guar, dextran 70, viscoelastics, and hyaluronic acid, as well as combinations thereof. Additional ingredients may include those routinely included in mouthwashes, nasal sprays, shampoos, soaps, and conditioners. Such components may be included in the formulations in varying percentages ranging from less than 0.1% to 99% w/w %, more preferably less than 1% to 10% w/w %. Other components which can be included in these pharmaceutical formulations include, but are not limited to preservatives such as Polixetonium, polyquaternium-42, Polyquaternium-1, Polyquat, Alkyl-hydroxy benzoate preservatives, parabens, hydrogen peroxide, benzalkonium chloride, cetylpyidimine chloride, cetalkonium chloride, sodium perborate, Purite, disappearing preservatives, Polyhexamethylene biguanide (PHMB), chlorobutanol, Benzododecinium bromide, "Ionic buffered system", povidone, silver, silver sulfate, betadine, and other antiseptics and proprietary and non-proprietary preservatives. Also, PLL-g-PEG, may act as a preservative. Antibiotics, antiviral agents (whether small molecule or biologics) may be contained in the formulation. In some embodiments, preservative free formulations are preferred.

Further, in some embodiments, the formulations and coatings may include one or more additional active pharmaceutical ingredients. Examples include, but are in no way limited to anesthetics, antibiotics, antivirals, antiinflammatory agents, intraocular pressure lowering agents, artificial tears, lubricating products, dilating agents, immunosuppressives, antiangiogenic agents, monoclonal antibodies, proteins, peptides, neuroprotectants, small molecules and antibodies. In some embodiments, the formulation is delivered prior to personal protective equipment use.

Some exemplary, without limitations, additional medications that can be included in these formulations include, as indicated for human benefit: antiviral agents including remdesivir, anti-retroviral agents, rimantadine and others selected from this list: Abacavir Use for HIV, Acyclovir (Aciclovir) Use for herpes e.g. Chicken pox, Adefovir Use for chronic Hepatitis B, Amantadine Use for influenza, Ampligen, Amprenavir (Agenerase) Use for inhibition of HIV, Arbidol, Atazanavir, Atripla (fixed dose drug), Balavir, Baloxavir marboxil (Xofluza), Biktarvy, Boceprevir (Victrelis), Cidofovir, Cobicistat (Tybost), Combivir (fixed dose drug), Daclatasvir (Daklinza), Darunavir, Delavirdine, Descovy, Didanosine, Docosanol, Dolutegravir, Doravirine (Pifeltro), Ecoliever, Edoxudine, Efavirenz, Elvitegravir, Emtricitabine, Enfuvirtide, Entecavir, Etravirine (Intelence), Famciclovir, Fixed dose combination (antiretroviral), Fomivirsen, Fosamprenavir, Foscarnet, Fosfonet, Fusion inhibitor, Ganciclovir (Cytovene), Ibacitabine, Ibalizumab (Trogarzo), Idoxuridine, Imiquimod, Imunovir, Indinavir, Inosine, Integrase inhibitor, Interferon type I, Interferon type II, Interferon type III, Interferon, Lamivudine, Letermovir (Prevymis), Lopinavir, Loviride, Maraviroc, Methisazone, Moroxydine, Nelfinavir, Nevirapine, Nexavir, Nitazoxanide, Norvir, Nucleoside analogues, Oseltamivir (Tamiflu), Peginterferon alfa-2a, Peginterferon alfa-2b, Penciclovir, Peramivir (Rapivab), Pleconaril, Podophyllotoxin, Protease inhibitor (pharmacology), Pyramidine, Raltegravir, Remdesivir, Reverse transcriptase inhibitor, Ribavirin, Rilpivirine (Edurant), Rimantadine, Ritonavir, Saquinavir, Simeprevir (Olysio), Sofosbuvir, Stavudine, Synergistic enhancer (antiretroviral), Telaprevir, Telbivudine (Tyzeka), Tenofovir alafenamide, Tenofovir disoproxil, Tenofovir, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), Zidovudine. Hydroxychloroquine, chloroquine, and azithromycin may be included in said formulations. Biomolecules selected from antibody products with poly or monoclonal, biomolecules that bid to antibodies, proteins, antigens are included in potential formulations. Fragments of antibodies, trap molecules, and biomolecules that bind to ADC's and other antibodies, cell receptors and proteins relevant to conditions addressed in this application are included, whether known, in development, or not yet developed or conceived. The key is a combination of the claimed copolymers formulated with another effective agent in management of the disease addressed to improve performance or efficacy—including synergistic therapies. Biomolecules are produced by a living organism. Synthetically produced antibodies, recombinant proteins, and other large and small molecules for which new techniques lead to new nomenclatures are also included. ACE2 receptor blockers, steroids (glucocorticoid, androgens, estrogens, etc.) are also potential formulations components, and are considered within various embodiments of the current invention.

pH of formulations of the present invention is in a physiologic range depending upon the site of administration and the site of the biological surface or membrane that is to be modified. Typically, the pH is above 3, e.g., above 5.6 and below 9.

Formulations may include new or established dry eye or corneal therapeutics including, but not limited to, cyclosporine, lifitigrast, LFA-antagonists, steroids including loteprednol, dexamethasone, flucinolone, difluprednate, aldehyde traps, fonaldepar, varenicline, visomitin, kinases, silk derived proteins, voclosporin, omega 3 fatty acids, and any demulcents or lubricants in the OTC monograph referenced completely herein. Importantly, some embodiments of the formulations have very low viscosity (lower than most artificial tear products on the market). This advantage is that vision is not blurred on instillation, sprays work easily through small diameter nozzles, and mouthwashes rinse out completely and easily and are well tolerated. Electrospray and other microelectronic and mechanical delivery systems, high precision multi-jet systems and other approaches to microdose release are included as possible delivery systems, among others. The copolymers reside following rising. The residual bioadhesive polymers of course already bind to the cells for which they protect. For example, the formulation in one test had a viscosity of 2.7 cP. Furthermore, the benefit conferred with these inventions demonstrates the value of the graft or block copolymer as the mechanism of effect.

As described in Example 1, In Vitro experiments, this approach is effective in reducing viral infectivity. In other examples, reduced ADC entry into epithelial cells and decreasing eye adverse event are shown.

Furthermore, as described in Examples herein, performance of these block and graft copolymer formulations is assessed in the eyes of human volunteers. Previous experiments have shown the eye drop was well tolerated. For example, of the multiple initial human exposures, there was no irritation or discomfort reported by any subject. Additionally, there were no reports of blur following single and repeated instillation of 50 microliters or less. Thus, a product with lower viscosity is an embodiment of this invention.

As will be understood by the skilled artisan upon reading this disclosure, however, alternative ophthalmic delivery means including, but not limited to, intraocular, periocular, conjunctival, subconjunctival, transconjunctival, peribulbar, retrobulbar, subtenons, transscleral, topical gel, topical dispersion, intraorbital, intrascleral, intravitreal, subretinal, transretinal, choroidal, uveal, intracameral, transcorneal, intracorneal, intralenticular (including phakia and psuedophakia), and in or adjacent to the optic nerve, can be used. The invention can be used with polymeric, and other delayed release formulations for prolonged drug delivery. The invention can be used with depot formulations. The invention can be intravenous to treat other ADC toxicities such as thrombocytopenia.

Of importance in the current invention for use in ADC toxicity and also for viral infection, there are in vitro and in vivo opportunities of commercial value and product development value. For example, since these copolymers with bioadhesive and passivation moieties are shown effective in these conditions both in vitro and in humans, their use in development has value. A cell may be treated with a copolymer formulation, and then ADC's can be added. Tissue culture can also be used including corneal epithelial models. Those that show less uptake in the setting of copolymer presence may be selected for development as there is a known ameliorating approach to off-target or macropinocytotic uptake. The models may use epithelial cell lines, harvested epithelial cells, megakaryocytes, other cells, and human umbilical vein endothelial cells. Cell types with risk for toxicity are used in some laboratory development procedures. Likewise, antiviral efficacy in treatments and preventive measures may be assessed in the laboratory/developmental setting of viral and copolymer exposures to select synergistic and optimal molecules and formulations for human development. Thus, a claim to treating a cell broadly is a pertinent and useful invention to advance therapies for human health addressed herein.

COVID 19, the infection caused by SARS-Cov-2 is a devastating disease for many patients with a death rate up to 3%, and many more infecting requiring hospitalization and ICU care. Millions of patients have been infected and death rates are continually increasing into the hundreds of thousands. More than 3 million global patients have been infected and over 200,000 deaths within a six-month period have occurred. Patients of older age and with pre-existing medical conditions are at higher risk for morbidity and mortality. High viral load exposures are also a significant risk for morbidity. SARS-Cov-2 has caused a global pandemic, and better, and alternative treatments are needed. New pandemics may also develop, and this approach is not specific to one viral strain, although the spike protein in SARS-Cov-2 is amenable to passivation with the graft copolymer and block copolymer approach.

"Viral infectivity" relates to the exposure of at-risk host cells to a pathogenic virus. Using protein receptor and other uptake mechanisms viral particles can enter a cell, release their RNA or DNA and hijack the cells protein manufacturing and nucleotide machinery or other metabolic processes to manufacture more viral particles which are then released to infect other cells and other organisms. Without being limited to any particular mechanism, a formulation comprising a graft copolymer as described above (cationic, hydrophobic, anionic, with hydrophilic side chains), such as PLL-g-PEG, adheres to the biological surfaces of viral particles (including the spike for SARS-Cov-2) or other cell entry mediating proteins on the lipid membrane shell of the virus, or on the viral particle generally. The charged, hydrophobic, or anionic moiety, PLL for example, moiety leads to the bioadhesion. The hydrophilic (e.g. PEG) moiety prevents and/or reduces the interaction with the target cell. When applied as a drop, spray mist, or rinse, the graft co-polymer is able to move from surface tissue to viral particle due to physical chemistry on-off bonding associated with electrostatic interactions. Passivation moieties can be non-ionic, nonionic, and inert, as well as hydrophilic. The graft copolymer also protects the cells at risk in a similar manner and directly interferes with receptor proteins in some cases (e.g. ACE2) to enhance activity. The combined exposures to viral particles and at-risk cells reduce substantially their interaction and viral infectivity. Decreased interaction is beneficial to cells, tissues, and organisms including humans by decreasing pathogen or toxin exposure, thereby decreasing morbidity and mortality associated with these agents. For example, lower viral loads can decrease the severity of subsequent infection and allow the host defenses better opportunity to work. Decreasing viral exposure reduces transmission rates and possibly the severity of viral infection. Accordingly, the method of reducing SARS-Cov-2 with infection as described herein will be an important additional approach to safely protect a subject.

Similar formulations have already been used in the eye with no adverse events, and are safe for oral, respiratory, and nasal passageway use. PLL-g-PEG is made from an amino acid and PEG. Extensive reviews show the formulations are safe for use in humans and animals.

These formulations can also be widely used in accordance with the present invention to reduce transmission of SARS-Cov-2 and novel viruses via nasal and inhalational applications in settings including, but in no way limited to, hospitals, emergency departments, intensive care units, airplanes, preschools and schools, homes of affected viral individuals, as well as nursing homes and chronic care facilities. Heath care workers, and first responders may also benefit. "Novel" or "new" viruses means those with mutations or general characteristics that demonstrate humans, generally—the majority of the population, does not have resistance through prior exposure or vaccines. "Transfection" means how the virus enters the host. "Epidemics" and "pandemics" are determinations made often by health authorities. Pandemic is disease prevalent over a country or the world at a particular time. Epidemic is a widespread occurrence of an infectious disease in a community at a particular time. The invention particularly relates to viral pandemic and COVID19. COVID19 is the viral illness caused by SARS-Cov-2. Herd immunity is the resistance to the spread of a contagious disease within a population that results if a sufficiently high proportion of individuals are immune to the disease, through vaccination or previous exposure to the virus resulting in the production of antibodies. Herd immunity requires resistance to a virus in significant numbers. Important utilities of the formulations exist for children and adults with infirmities, such as immunodeficiencies, chronic disease and other chronic conditions such as cystic fibrosis, which leave the host more susceptible to routine illness.

Corneal epithelial microcyst like epitheliopathy is recently identified problem known to be associated with and/or due to ADC treatment, and it has recently become important clinically as ADC's with corneal epithelial toxicity are entering commercial use after many years of development. ADC's are under development as an effective therapeutic for many forms of oncologic disease. These are costly and resource demanding development programs, and the need to limit use due to ophthalmic toxicity is significant. At times human toxicity isn't manifest until clinical trials. It is important to allow patients to maintain ADC therapy for optimal oncologic (or other indicated) disease outcomes (survival or progression free responses, beneficial effect) and corneal epithelial toxicity is an adverse event that can limit therapy or even cause patients to discontinue ADC-related therapy. Significant ophthalmic and other types of adverse events associated with ADCs are a problem for patients and treating physicians. The payload or warhead is thought to cause the adverse events (ophthalmic or in some embodiments otherwise such as other cells or cells in culture or tissue culture) following its release (cleavage of the linker) from the ADC once in the cell.

Without being bound to a particular theory or mechanism of toxicity, but as a method to explain the presumed utility of this invention for which the discovery of benefit is demonstrated in vitro and in vivo.

ADC's are able to gain exposure to the eye through one of two ways based on the toxicity seen clinically. First, the ADC may get to limbal stem cell daughter cells and eventually basal stem cells and basal epithelial cells via release from the perilimbal circulation (including but not limited to the palisades of Vogt which have a distinct vasculature with narrow, barely visible, arterial and venous components of radially oriented hairpin loops) into the extracellular space and subsequent non-specific uptake by basal cells that then move into the cornea.

"Macropinocytosis" has been described as a mechanism for ADC's to enter cells such as the corneal cells affected by the toxicity as they typically lack the specific receptor that the antibody portion of the ADC uses to enter the cell. Thus, the entry of the ADC into the cell is nonspecific and can be considered off target. Embodiments of the inventions herein ameliorate or reduce off target ADC-induced corneal cell toxicity including limbal stem cells, daughter cells, transient amplifying cells, wing cells, basal cells, corneal epithelial cells, and terminal epithelia differentiated cells.

The ADC may also gain exposure to the cornea via the tears. Drugs have been reported to be secreted in tears. Cytokines of many kinds have been identified in the tears where the secretion from the lacrimal system is suggested path to their presence. The tear film contains hundreds of proteins and/or enzymes, secretion by lacrimal glands again is the understood mechanism. The leakage from the plasma either across the blood/tear barrier or by leakage from tissue interstitial fluid has also been described as paths to protein presence in tears. Antibodies are found in tears.

The superficial corneal epithelial cells have no blood supply and must obtain fluid replenishment or nourishment in some manner independent from a direct blood supply. Epithelial cells use macropinocytosis as a method of nourishment. The plasma membranes of cells contain combinations of glycosphingolipids, cholesterol and protein receptors organized in glycolipoprotein lipid microdomains termed lipid rafts. Lipid-raft internalization is a process documented in corneal epithelial cells for the internalization of extracellular material. Macropinocytosis is a type of endocytosis whereby extracellular material is captured by a cell. (Macropinocytosis is a means by which eukaryotic cells ingest extracellular liquid and dissolved molecules. Pinocytosis may be used as a term herein in embodiments as well. Pinocytosis is the ingestion of liquid into a cell by the budding of small vesicles from the cell membrane. Micropinocytosis is considered herein and may be used as term in embodiments as well and can be used in any specified embodiment where either macropinocytosis or pinocytosis generally are used. Micropinocytosis is the incorporation of macromolecules or other chemical substances into cells by membrane invagination and the pinching off of relatively minute vesicles.) Toxins and pathogens utilize endocytosis and macropinocytosis to gain entry into many cell types. ADC's can get into cells by macropinocytosis.

Macropinocytosis occurs in many types of cells. It has been shown that macropinocytosis is a method for ADC entry into corneal epithelial cells. These methods of cellular uptake of extracellular components are natural; there inhibition in select settings is, however, beneficial. Macropinocytosis is a likely method for superficial epithelial cells internalizing ADCs. Being the least specific pathway, it is directed by actin-driven membrane protrusions which create large endocytic vesicles known as macropinosomes. Eventually, those vesicles fuse with lysosomes. Once an ADC is within a lysosome, the payload, specifically in the setting of ADV tox, maytansinoid and auristatins are associated with toxicity. However, tubulin inhibiters generally are potentially causative of corneal toxicity. The exposure to the cells most adversely affected by the toxic payload generally, or tubulin inhibitors specifically are cells that either divide (mitotic activity that is microtubule dependent) or migration (also microtubule involvement.

Payloads are the cytotoxic molecule that is linked to an antibody which is subsequently cleaved at the linker by intracellular enzymes. It is the method by which ADC's deliver a toxin to target (neoplastic) cells, but other cells are also adversely affected, and the ADC's can gain entry even without expressing an ADC interacting receptor/protein. Pinocytosis is a means ADC's enter cells. Other payloads besides tubulin inhibitors may show corneal epithelial toxicity, and those alternatives cytotoxic payloads are considered herein. Once the payload is cleaved from the ADC, it actively performs its chemical function such as the inhibition of polymerization of tubulin into microtubules which are needed for cell division, and in some cases cell migration. The presence of tubulin inhibitors in a dividing cell can cause cell death (followed by apoptosis and pyknosis). Apoptosis and pyknosis have been observed in corneal epithelial cells in ADC toxicity. The pyknotic cells are presumed to be the cause of the examination finding of microcyst like keratopathy. The dead or dying, and dysfunctional cells are seen in the epithelial layer on slit lamp examination. The extent can be quantified.

It is possible that once cleaved in a cell that uptakes the ADC, that the cytotoxic molecule may be released from said cell and cause a bystander effect. Thus, reducing cellular uptake and cleavage may be an intervention that has an excess relative reduction (greater number of cells may be protected than actually-uptake the ADC into one cell-due to bystander death). Bystander death means release of the cytotoxin, once cleaved into the extracellular space where it then enters subsequent cells. It thus may move through the corneal epithelial layers once engulfed by a more superficial cell. It also may be released at the limbus once taken up by a stem cell and released into other nearby stem cells and diffuse inward into basal stem cells. Such diffusion of the cytotoxic agent may be reduced with the methods of this invention. Not only may the approach reduce uptake and cleavage, but polymer may limit the movement and re-uptake of local cytotoxin. Regardless of the mechanism, the effect is real and valuable.

Toxicity in the human is or may be in certain cases confined to the epithelial layers (not involving the stroma or endothelium). [Note the stroma or endothelium may be involved secondarily or in some ADC designs). Normal replenishment of superficial epithelial cells is interfered with and the superficial epithelial layer becomes abnormal and can manifest with punctate staining, corneal epithelial defects, and abnormal refracting surfaces. Visual acuity is adversely affected in many cases. The patient may develop symptoms such as blurred vision, dry eye, corneal foreign body sensation, ocular discomfort, ocular irritation. Corneal infection, stromal keratitis, and ulcerative keratitis have been reported with ADC therapy. These are all significant adverse events and dose holds and dose delays are not infrequently required due to these toxicities. Histopathologic examination in cases of cytarabine (a similar situation to cases encountered with some ADCs) eye shows profound degeneration of the rapidly dividing basal epithelial cells, which leads to formation of epithelial microcysts.

Ocular irritation is an ADC related toxicity or adverse event, but not the only symptom. Corneal superficial punctate epitheliopathy, corneal erosions and epithelial defects, corneal ulcers, corneal infections, corneal perforations, can or potentially can occur from ADC induced corneal toxicity. Foreign body sensation and reduced visual acuity can occur. Dose holds, dose delays, and dose reductions for this life saving treatment can be required. Patients need vision for driving and reading. Vision is a high driver of quality of life. Allowing patients to maintain a more regular dosing schedule as well as minimizing eye symptoms is a benefit of this invention. Patients will have fewer and less severe adverse events leading to better outcomes from less uninterrupted ADC.

ADC related corneal toxicity has no treatment directed at the mechanism as demonstrated herein. Symptomatic management is the extent of the interventions. Commercially available lubricant eye drops, punctual occlusion, bandage contact lenses help with symptoms.

In one aspect, a method to decease the adverse events associated with antibody-drug conjugate usage in the setting of an off-target uptake pathway (but not limited to off-target uptake pathways necessarily) that is causing damage to nonneoplastic cells, by applying an effective amount of a copolymer with electrostatic and steric mediating properties applied to cells that are affected by said toxicity.

Without being bound to any particular theory, the utility of the invention can be manifest through interferences, mitigations, and inhibitions as described herein.

Another related approach managing ADC toxicity that occurs locally through off target uptake is to use an antibody to the ADC itself. The Antibody crafted toward the specific ADC will be designed to with a passivation moiety such as pegylation that would thereby decrease the ability of the ADC to enter cells via macropinocytosis. The ADC will, for example, be delivered locally to inhibit pinocytotic uptake. Antibody may be pegylated or have other passivation moieties as described herein using modifications to the antibody against the ADC by joining it to hydrophilic polymers for use in cell culture, labs, and in vivo, humans. Use in the laboratory is important because in embodiments where copolymers or antibodies are shown to reduce ADC related toxicity or other drug corneal toxicity, clinical development can be pursued with less risk for eye adverse events that complicate therapy.

The cationic graft copolymers interfere with cellular (corneal epithelial cell) uptake of the ADC. This unique methodological approach allows for improved corneal epithelial health and improved examination and symptomatic findings and decreases ocular risk. Reduced ADC-related cell death (e.g. toxicity) has many benefits. There are intravenous and other opportunities for toxicity reduction, thus claims are directed broadly. Megakaryocytes can use macropinocytosis to internalize ADC's and thus the opportunity to decrease this known adverse event associated ADC's is addressed with this invention.

Epithelial cells are known to have negative charges ($3.6*10^{-4}$) on the surface. Thus, the cationic graft and block copolymers passivate these negative charges which may play a role in ADC uptake. Evidence exists that making an ADC positively charged increases toxicity, and making it negatively charged decreases uptake. The key for this invention is the finding that passivation through electrostatic (or in some embodiments hydrophobic) interactions is beneficial. By decreasing the ADC's interaction at the cell surface, in one embodiment, ADC entry is reduced. By protecting the cell generally, ADC toxicity is reduced, as well. Other (non epithelial) cells have charged areas (and hydrophobic areas) allowing for these interaction reduction interferences, as well. The copolymer also may act at key protein components on the cell and ADC to limit uptake.

It also relevant that there are multiple methods for getting the cationic graft copolymer (or other effective block or graft copolymer) to the target tissue. PLL-g-PEG has been shown safe for mammalian IV infusion. Eye drops and topical exposures have been shown safe. The polymer can reach the target limbal cells via intravenous infusion. Subconjunctival delivery is also a potential valuable approach to ameliorating toxicity as this approach provides both a reservoir and an approach to the limbal stem cells and the daughter cells including basal epithelial cells. The conjunctiva is also somewhat permeable to macromolecules. The intercellular spaces in the conjunctival epithelium are wider than cornea and therefore more permeable to larger molecules. Thus, topically delivered, PLL-g-PEG can gain access to the stem cells (precursor cells to corneal superficial epithelial cells) and reduce toxicity by interfering with ADC corneal toxicity. Topical delivery to the cornea (or eye) can interfere with any ADC that gains entry to the superficial corneal or conjunctival epithelium. Thus, the release of the payload and its subsequent movement through the 5 or 6 corneal layers to basal cells is reduced. Also, larger molecules can naturally gain entry into the superficial epithelium. Thus, PLL-g-PEG or other identified and claimed graft or block copolymers can protect basal epithelial cells which are deeper in the epithelial layer. They have access to this space. Likewise, an ADC may gain exposure to deeper corneal epithelial cells. The copolymer thus can interfere at the ADC to block interaction with cell capture processes and also interfere on the corneal cell surface to interfere with ADC entry into cells. These effects lead to an effective approach to reducing ADC related corneal toxicity. In the case of the corneal cells, the basal, and other potentially adversely affected cells are protected and show, to some measurable degree less toxicity and patients demonstrate fewer signs and symptoms of ADC corneal toxicity. The opportunity is profound and applies to other approaches to minimizing off-target ADC toxicity. The corneal cells typically do not exhibit receptors for which the ADC is targeting, thus the toxicity is off target. In some embodiments, if there is a component of on target uptake based on the presence of a receptor on the corneal cell, these copolymers may be of benefit with a local application.

Delivery can be local, regional, or systemic. Many formulations exist. The copolymer (PLL-g-PEG) can decrease exposure of corneal tissue to the ADC an also reduce uptake. The interference is steric and charge based. By passivating the ADC and passivating the cell surface, uptake is reduced. The active charged or hydrophobic moiety adheres to the cell or ADC. The hydrophilic component of the polymer reduces ADC—corneal interactions and reduces uptake. Binding to conjunctiva or cornea by the copolymer can also serve as a reservoir for eventual interference and passivation of the ADC as it moves from the tear film into the lacrimal drainage system. The copolymers selected are nontoxic. Concentration in eye drops can range from 0.01 to 10% but are more commonly 0.5 to 3% w/w. Subconjunctival formulations may be of higher concentration.

The graft copolymer tested is PLL(20)-g[3.5]-PEG(5) in one experiment, but other molecular sizes and grafting ratios are safe and effective.

Formulations described herein also provide a safe, at some point, it may be beneficial to include other drug or polymer components in an eye drop for ADC-toxicity mitigation or viral protection. Subconjunctival delivery may require less frequent dosing. Topical delivery is compatible with long term use. A preservative is avoided in many embodiments to help protect the corneal surface and not harm epithelial cells otherwise. Exemplary additional active pharmaceutical ingredients for ophthalmological uses include, but are not limited to, lubricants and demulcents and sterile water and other standard excipients. There may be a benefit to combine with another active agent in some embodiments including novel protective agents for which a synergy with copolymers may exist. Also, antibiotics (fluoroquinolones, vancomycin, cephalosporin, gentamycin, erythromycin, azithromycin, sulfa drugs, bacitracin, gatifloxacin, levofloxin, moxifloxacin, ofoxacin), acetazolamide, antazoline, aspirin, atropine, azelastine, bacitracin, betaxolol, bimatoprost, botanical drugs including zeaxanthine lutein, lycopene brimonodine, brinzolamide, carbachol, carteolol, ciprofloxacin, ofloxacin, cromalyn, cyclosporine, dapiprazole, dexamethasone, diclofenac, dipivifren, dorzolamide, epinephrine, erythromycin, fluoromethalone, flurbiprofen, gentamycin, glaucoma medications (prostaglandins, carbonic anhydrase inhibitors, epinephrine or alpha-agonists, beta-blockers), gramicidin, homatropine, hydrocortisone, hyoscine, keterolac, ibuprofen, ketotifen, latanaprost, levobunolol, levocabastine, levofloxin, loteprednol, medrysone, methazolamide, metipranolol, naphazoline, natamycin, nedocromil, neomycin, neuroprotective agents, nonsteroidal anti-inflammatories, nepafanec, norfloxacin, ofloxacinm olopatadine, oxymetazoline, pemirolast, pheniramine, phenylephrine, pilocarpine, povidone, prednisolone, proparacaine, scopolamine, tetracaine, steroids, sulfacetamide, tetrahydrozoline, hypertonic tears, timolal, tobramycin, travaprost, trifluridine, trimethiprim, tropicamide, unoprostone and zinc—all may have some value in a co-formulation. Prodrugs and related compounds, as well as any new active pharmaceutical ingredients can be used with the block and graft copolymers here described to reduce ADC-toxicity or better manage ADC-related adverse events.

Based on the mechanism and non-specific protective and passivation approach, and ADC with a tubulin inhibitor or epithelial cell toxic agent is mitigated with this copolymer based approach. The following ADC's are claimed in this invention, but in no way is this list limiting. Copolymers discussed herein can be formulated with the ADC itself, or separately. The toxic payload may be a maytansinoid or an auristatin but may be another type generally, or another tubulin inhibitor. Tubulin inhibitors, and inhibitors of tubulin polymerization have specific utility in the current embodiments. Tubulin inhibitors may include but are not limited to: paclitaxel, epothilone, docetaxel, discodermolide, colchicine, combrestatin, 2-methoxyestradiol, methoxy benzenesulfonamides (E7010), vinblastine, vincristine, vinorelbine, vinfluine, dolastatins, halichondrins, hemiasterlins, cryptophysin 52, paclitaxel sites, *vinca* alkaloid sites, colchicine sites, etc. are considered. It may be a tubulin disruptor or work by other cytotoxic mechanisms. DNA synthesis inhibitors such as cytarabine are included. Other antineoplastic agents that can serve as payloads including Monomethyl auristatin E (MMAE), DM1 (mertansine), T-DM1, Maytansinoids, auristatins, DUO Duostatin-5 and other Duostatins, AF-HPA (auristatin F-hydroxypropylamide), PBD (Pyrrolobenzodiazepines), MMAF (Monomethyl auristatin F), Calich, caliche, calicheamicin, DM4

(Ravtansine), SN-38, Irinotecan metabolite, PF063801 01, Dxd, DNA topoisomerase I inhibitor, DOX, doxorubicin, PF063801 01, mitoxantrone, etoposide, tesirine, PBD dimer, Pyrrolobenzodiazepine, SG3199. Toxins Targeting Tubulin Filaments, toxins Targeting DNA, toxins Targeting RNA, Nanocarriers, Protein Toxins, and enzymes are considered.

Varying linkers in ADC drugs are claimed, both known in 2020, and those that will be developed are embidiments when utilized with protection or treatment from toxicity through copolymer utilization in models or clinically. Embodiments also include use with ADC's noted below: Gemtuzumab ozogamicin, Brentuximab vedotin, Trastuzumab emtansine, Inotuzumab ozogamicin, Polatuzumab vedotin-piiq, Enfortumab vedotin, Trastuzumab deruxtecan, IMGN242 (huC242-DM4), CanAg/DM4/SPDB, IMGN242 (huC242-DM4), CanAg/DM4/SPDB, Trastuzumab emtansine, (T-DM1), SAR3419 (huB4-DM4), SGN-CD19A, CD19/MMAF, (auristatin)/mc AVE9633, belantomab mafodotin, CD33/DM4/SPDB, CD70/MMAF (auristatin SGN-75 CD70-positive CD70/MMAF (auristatin)/mc, SAR566658 CA6+, DS6/DM4/SPDB, CD33/calicheamicin/
Hydrazine, Ephrin type A receptor 2 (EphA2)/mcMMAF (auristatin)/mc, Lorvotuzumab, mertansine, D56/DM1/SPP, CD138/DM4/SPDB, FRa/DM4/SPDB, AGS-16M8FMMAF,
AGS-16C3FMMAF, ENPP3/MMAF (auristatin), as well as, without being limiting:

A166 ADC
AB-3A4 ADC
ABBV-176 (ABV176)
ABBV-321
ABBV-3373
AbGn-107 (Ab1-18Hrl)
AbGn-108
AbGn-110
ADCT-502
ADCT-601
ADCT-602 (hLL2-cys-PBD)
ADCT-701
AGS-16C3F (AGS 16C3F/AGS-16M8F)
AGS-16M8F (AGS 16C3F/AGS-16C3F)
AGS62P1
ALT-P7
AMG 224
AMG-595
AMG172
Anetumab corixetan
Anetumab Ravtansine|BAY 94-9343
Anti-ADAMS ADC (Anti-ADAMS-sulfoSPDB-DM4)
Anti-ADAMS ADC (Anti-ADAM9(C442)-DGN549)
Anti-CD19 ATAC (anti-CD19 ADC)
Anti-CD22-NMS249
Anti-CD70-ADC (CD70-ADC)
Anti-cMET ADC (CBT-161)
Anti-endosialin-MC-VC-PABC-MMAE
Anti-ETBR (RG-7636)
anti-HER-3 ADC
anti-TEM-1 Antibody-Drug Conjugate (TEM-1-ADC).
Anti-TM4SF1 ADC
Aprutumab ixadotin|BAY 1187982
AR-001|YBL-001
ARX517-PSMA-ADC
ARX788 HER2 ADC|ARX788
ASG-22CE
ASN-004 (ASN 004)
AVID100
AVID300|AVID 300
Azintuxizumab Vedotin|ABBV-838
Azonafide-ADC
BA3011|CAB-Ax1-ADC (CAB-anti-Ax1-ADC)
BA3021|Anti-ROR2 ADC|CAB-ROR2-ADC
BAT8001
BAY79-4620
BDC-1001
Belantamab mafodotin|GSK2857916|J6M0-mcMMAF
BIIB-015|BIIB015
Bivatuzumab mertansine|Anti-CD44v6-DM1|BIWI-1
BL-B029A1
B L-M002A2
BL-M005A2
Brentuximab vedotin|SGN35|Adcetris®
Bstrongximab-ADC
BT1718 (BT 1718)
c-MET ADC
Camidanlumab tesirine|ADCT-301|HuMax-TAC-ADC
Cantuzumab mertansine|huC242-DM1|SB-408075
Cantuzumab Ravtansine|IMGN-242
CC-99712—Anti-BCMA ADC
CD184-Dasatinib (CD184-Dasatinib-ADC)
CD184-FK506
CD22-4AP
CD70-glucocorticoid ADC
CDX-014
Cetuximab sarotalocan|ASP-1929|RM-1929
Cirmtuzumab Vedotin|UC-961ADC3
Clivatuzumab Tetraxetan
CMB-401|hCTMO1-calicheamicin|CDP-671
Cofetuzumab pelidotin|PF-06647020
Coltuximab Ravtansine|SAR 3419
CX-2009
Cymac-001 (anti-CD163-dexamethasone ADC)
D3-GPC2-PBD (anti-GPC2 ADC)
DEDN6526A (RG-7636/RG7636)
Denintuzumab mafodotin|SGN-CD19A|SGN-19A|hBU12-491
Depatuxizumab Mafodotin|ABT-414
Derlotuximab Biotin
DHES0815A
Disitamab Vedotin|RC-48|RC 480-ADC|RC48
DMOT4039A (DMOT-4039A/RG7600/RG 7600)
DS-1062 (TROP2 ADC)
DS-7300 (B7-H3 ADC)
DSTA4637S (Anti-*S. aureus* TAC; RG7861)
EC1169
EC2629
EDC1 (DYS-ADC)
EDC9 (EDC-CD20)
EDO-772P/B776
EDO-B278
Enapotamab vedotin|HuMax-AXL-ADC|AXL-107-MMAE
Enfortumab Vedotin|ASG-22ME|ASG-22MSE
EP-400
Epitumomab cituxetan
Epratuzumab—SN-38
EV20/MMAF
Gemtuzumab ozogamicin|Mylotarg®
Glembatumumab vedotin|CDX-011
GM103
GTB-1550|OXS-1550|DT2219ARL
HDP-101 (Anti-CD269-ADC; Anti-CD269-amanitin-ADC)
Hertuzumab Vedotin HKT288 (CDH6-ADC)
HTI-1511
HuMAB-5B 1-ATAC
Ibritumomab tiuxetan
IGN523
IGN786
IKS01
IKS02
IKS03
IKS04
Iladatuzumab vedotin|DCDS0780A|R07032005
IMAB027-vcMMAE
IMAB362-vcMMAE
IMB-201
IMB-202
IMGN 289
IMGN 779|IMGN779
IMGN-242
IMGN-388
IMGN-633 (AVE9633)
IMGN632|IMGN 632
IMMU-140 (anti-HLA-DR-SN-38 ADC)
Indatuximab Ravtansine|BT-062
Indusatumab Vedotin|MLN-0264|TAK-264
Inotuzumab ozogamicin (CMC-544)|BESPONSA®
IPH43
KTN0125
KTN0182A
Labetuzumab govitecan|IMMU-130
Ladiratuzumab vedotin|SGN-LIV1A|Anti-LIV-1 ADC
Laprituximab emtansine|IMGN-289|IMGN289
LCB14-0110 (Herceptin-LC-LBG-MMAF)
LCB14-15 nm
LCB14-15xx
LCB14-15xx (NNV019)
LCB14-17nn
LCB14-19 nm
LCB14-2 nm
Lifastuzumab Vedotin|RG-7599|DNIB0600A
Lilotomab satetraxetan
Loncastuximab tesirine|ADCT-402
LOP628 (LOP-628)
Lorvotuzumab mertansine|IMGN-901
Losatuxizumab vedotin|ABBV-221
Lupartumab amadotin|BAY 1129980
LY3076226
MDX-060/iratumumab
MDX-1203|BMS936561
MEDI-547
MEDI3726|ADCT-401
MEDI4276 (MEDI 4276)
MEN1309|OBT076
MGC018; Anti-B7-H3 ADC
MI130004
Milatuzumab doxorubicin (hLL1-DOX|IMMU-110)
Mirvetuximab Soravtansine|IMGN-853
Mirzotamab Clezutoclax|ABBV-155
MLN-2704|MLN2704
MM-302
MORAb-202
Naratuximab emtansine|IMGN529|K7153A|Debio 1562
NBE-001
NBE-002-ROR-1
NBE-003
NC-6201 (ADCM-E7974)
NV101 (Doxorubicin-anti-CD99)
NV102 (Doxorubicin-anti-CD19)
NV103 (Irinotecan-anti-CD99)
OBI-999|Anti-Globo H ADC
OMTX503 (Anti-MTX3:Nigrin Immunoconjugate)
OMTX705 (Anti-MTXS:Cytolysin ADC)
Patritumab Deruxtecan
PCA062 (PCA-062)
PEN-221
PF 06263507 (A1-mcMMAF|Anti-5T4 monoclonal antibody|PF-06263507 PF06263507)
PF-06647263 (anti-EFNA4-ADC)
PF-06650808 (Anti-NOTCH3 ADC)
PF-06664178|PF06664178|PF 06664178
PF-06688992|PF06688992
PF-06804103 (Anti-NG-HER2 ADC)
Pinatuzumab vedotin|RG-7593|DCDT2980S|DCDT-2989S
Polatuzumab vedotin|Polivy™|RG-7596|DCDS4501A|DCDS-4501A
Praluzatamab Ravtansine
PSMA-ADC
Q5-Drug Conjugate
REGN2878-DM1 (Anti-PRLR-ADC)
RG-7598 (DFRF 4539A/RG7598/RG 7598)
RG-7841 (Anti-Ly6E/DLYE5953A)
RG7986
Rolinsatamab talirine
Rovalpituzumab tesirine|Rova-T|SC0001
Sacituzumab govitecan|IMMU-132|hRS7-SN38
Samrotamab Vedotin|ABBV-085|PR-1498487-MMAE
SAR 566658 (SAR566658)
SAR408701|SAR 408701
SAR428926
Satoreotide tetraxetan
Satumomab Penditide (OncoScint® CR/OV)
SC-006
SC16LD6.5
Serclutamab Talirine
SGN CD70A|SGN-CD70A (superseding SGN-75)
SGN-15|BMS-182248|BR96-DOX
SGN-CD123A
SGN-CD19B
SGN-CD352a
Sirtratumab vedotin (ASG-15ME)
SNG-8023 ADC
Sofituzumab vedotin|Anti-MUC16 ADC|RG7458|DMUC5754A
ST1
STRO-001 (Anti-CD74-ADC)
STRO-002
Tabituximab Barzuxetan|OTSA-101-DTPA
Tacatuzumab Tetraxetan
Tamrintamab Pamozirine|Anti-DPEP3 ADC
Telisotuzumab Vedotin|ABBV 399|ABBV399
TGM-001
TGM-002
TGM-003
TGM-004
TGM-005
Tisotumab Vedotin|HuMax®-TF-ADC
Trastuzumab deruxtecan (DS-8201, DS-8201a)
Trastuzumab duocarmazine|SYD985
Trastuzumab Emtansine|T-DM1|Kadcyla®
TRPH-222 (CD22-4AP)
U3-1402|HER3 ADC
Vadastuximab taurine|SGN-CD33A
Vandortuzumab vedotin (RG7450; DSTP3086S)
VIS705

Vorsetuzumab mafodotin (SGN-75)
VYNFINIT®|Vintafolide (EC145/MK 8109)
XMT-1522|TAK-522
XMT-1536
ZVO5-ADC (5T4-MMAF ADC)
ZV203

New and as yet undescribed publicly ADC's with the potential for corneal toxicity may be treated with the methods of this invention.

Minimization of cytarabine corneal toxicity is also claimed as there is uptake of the molecule with a positive charge on the nitrogen, and PLL-g-PEG and other cationic graft copolymers can minimize this charged interaction by passivating negative charges on surface cells.

Based on physical chemistry the copolymers will be effective in embodiments herein because said copolymer will have access to the drug (pharmaceutical), solution bathing the cells at risk, and the cells themselves creating a dynamic protective environment. When applied as a drop, suspension, solution, controlled delivery system or powder (possibly lyophilized), the graft co-polymer is able to move from surface tissue to ADC or other pharmaceutical in solution or tears or extracellular fluid due to physical chemistry on-off bonding associated with electrostatic or hydrophobic interactions.

From experiments described herein, it is expected that formulations of the present invention will also be useful for preventing viral infection or ADC uptake or interaction with target cells including, but not limited to, skin, mucous membranes (eye, nasal, oral) and hair. These formulations can thus also be applied in accordance with the present invention to epithelial tissue of the eye, respiratory tract, and gastrointestinal tract, mucous membrane, exposed wound surfaces, corneal and conjunctival surfaces, skin, and surgical and traumatic wounds and ulcerations. These formulations can serve to protect skin and other organs from viral infection and unwanted ADC interaction. Benefits can include reduction in rate of infection, less severe infections, and reduction in corneal epithelial toxicity. The copolymer may interact with both the infective agent or pharmaceutical and the surface of the cell at risk to passivate any interaction and provide a protective effect.

For these uses in humans, the formulation may be in the form of a lotion, gel, liquid, spray, rinse, dissolvable wafer, or glycerin bar to which water is added to solubilize the graft co-polymer or block co-polymer to make it more amenable to application. Formulations can be provided as individual, or single use products or in volumes for industrial use and/or multiple use dispensers. In addition to the graft or block co-polymer, such formulations may comprise any and all typical binders, excipients, and components found in cosmetic sprays, lotions, soaps, shampoos, cleansers, and oral, nasal, and eye care products.

Formulations can also be used in accordance with the present invention on animals, including household pets, to decrease viral infection or ADC toxicity.

Other uses for these formulations will become evident to those skilled in the art upon reading this disclosure and are such uses are encompassed by the present invention.

Extended-release formulations may prove particularly beneficial and herein are encompassed.

PLL-g-PEG is an example of a copolymer with bioadhesive and passivation moieties. PLL-g-PEG uses electrostatic bioadhesion with the cationic backbone. Hydrophobic and anionic moieties utilize alternative bioadhesive interactions (hydrophobicity, anionic). Formulations of said copolymers are safe for human use.

The following nonlimiting examples are provided to further illustrate the present invention. Percentages are weight/weight percent.

It has been described that drugs may be secreted in tear fluid. From: Lee, Brian A., et al. "Clinical and Histological Characterization of Toxic Keratopathy From Depatuxizumab Mafodotin (ABT-414), an Antibody-Drug Conjugate: [RETRACTED]." Cornea (2018). Note: Microcyst-like epithelial keratopathy (MEK). Regarding MEK: "Steroid is not an adequate treatment." And: " . . . confocal microscopy was notable for multiple large, round, hyperreflective lesions throughout the epithelium that seemed to correlate with MEK seen clinically. Histologically, the microcysts seem to correlate with engulfed apoptotic cells throughout the epithelium. In addition to the increased apoptotic cells noted in the histological specimens, immunohistochemistry revealed IgG-positive intracytoplasmic granules in the basal epithelium. Because depatuxizumab, the antibody component of ABT-414, is a monoclonal IgG1, it suggests that ABT-414 itself is deposited within the basal epithelium. The presence of ABT-414 directly in the epithelium in turn likely explains the increased apoptosis seen on histology."

Experimental techniques adapted from: Zhao, Hui, et al. "Modulation of Macropinocytosis-Mediated Internalization Decreases Ocular Toxicity of Antibody—Drug Conjugates." Cancer research 78.8 (2018): 2115-2126. Study design for cell culture: "Cell lines and reagents. All cells were maintained according to vendors' protocol. Human primary corneal epithelial cells (HCEC) from Life Technologies (catalog no. C018-5C) were cultured in keratinocyte-SFM (catalog no. 17005-42), and HCEC cells from ATCC (catalog no. PCS-700-010) were cultured in corneal epithelial cell basal medium (catalog no. PCS-700-030) supplemented with corneal epithelial cell growth kit (catalog no. PCS-700-040). Human umbilical vein endothelial cells (HUVEC, catalog no. C-003-5C) and human dermal fibroblasts, adult (HDFa, catalog no. C-013-5C) were from Life Technologies. HUVECs were grown in Medium 200 supplemented with low serum growth supplement (LSGS, catalog no. S-003-10). HDFa cells were grown in Medium 106 supplemented with LSGS. KU812 cells were from ATCC (catalog no. CRL-2099) and were grown in RPMI1640 plus 10% FBS as described previously. Cell lines were passaged in our laboratory for fewer than 6 months after their resuscitation. Human cell lines were confirmed utilizing short tandem repeat profiling (Promega) and confirmed to be *Mycoplasma* negative. Reagents for human hematopoietic stem cells (HSC) and their differentiation to megakaryocytes were reported previously. T-DM1 (Kadcyla; Genentech/Roche) was purchased (Myoderm). Macropinocytosis HSCs (105 cells/well) were grown in 24-well plates overnight and then incubated with 1 mg/mL dextran-FITC (10,000 MW, Life Technologies) for 3 hours at 37_C or 4_C as control. Cells were detached with trypsin and neutralized with neutralization solution (Life Technologies, catalog no. R002100). Cells were then washed three times with FACS stain buffer (FBS, BD Pharmingen, catalog no. 554656) and analyzed by Attune acoustic focusing cytometer (Life Technologies). To test the effect of 5-(N-ethyl-Nisopropyl) amiloride (EIPA), indicated amount of EIPA was added to cell culture 30 minutes prior to dextran-FITC addition. Median fluorescence intensity ratio (MFIR) was derived from MFI values at 37_C normalized against those at 4_C. Proliferation assays HCECs (500 cells/well) and HUVECs (2,000 cells/well) in 100 mL were seeded in collagen-coated 96-well plates (Corning, catalog no. 354650), and HDFa (2,000 cells/well) and KU812 (2,500 cells/well) in 100 mL were grown in 96-well tissue culture plates (Corning assay plate, catalog no. 3903). After treatment with ADCs for 6 days, CellTiter-Glo (CTG) luminescence assay kit (Promega, catalog no. G7572) was used to measure the viability of the treated cells relative to control. CTG values were normalized against mock-treated cells at day 6 (% max proliferation), and GraphPad Prism 6 was used to generate IC50 values using a sigmoidal dose—response (variable slope). Assay plates contained technical triplicates for each drug concentration, and data presented are the mean of at least two independent determinations. ANS assay ADCs (2 mg/mL) were prepared in PBS, and 1:2 serial dilutions were made in a black-walled, 96-well plate. Equal volume of 1,8-ANS (1-anilinonaphthalene-8-sulfonic acid, Thermo Fisher Scientific, catalog no. A47) was added and incubated for 30 minutes at room temperature. Fluorescence signal was measured (ex. 390 nm/em. 470 nm). Hydrophobicity index was the slope from the linear regression analysis. Confocal microscopy Cells were seeded on 8-well chamber slides (0.75 105 cells per well) and cultured for 48 hours prior to treatment and subsequent immunostaining. Cells were then incubated with AGS-16C3F with and without coincubation of 0.5 mg/mL Dextran-Texas Red (Molecular Probes; D18653) for 4 hours at 37 C. Inhibition of macropinocytosis was evaluated by treating cells with EIPA for 30 minutes prior to AGS-16C3F/Dextran-Texas Red incubation. After the incubation period, unbound antibody was washed off with PBS and cells were fixed in 4% paraformaldehyde for 20 minutes at room temperature. Cells were then permeabilized in PBS plus 0.1% Triton-X-100 for 15 minutes, and nonspecific labeling was blocked in PBS plus 10% normal goat serum. Cell surface—bound and internalized cytosolic AGS-16C3F was visualized by incubating cells with Alexa Fluor 488—labeled goat anti-human IgG (Thermo Fisher Scientific, catalog no. A-11013). Nuclei were visualized with TO-PRO-3 Iodide (Thermo Fisher Scientific, catalog no. T3605), and coverslips were mounted using ProLong Gold Antifade reagent (Thermo Fisher Scientific, catalog no. P36934) for imaging. High-resolution laser confocal image sections were acquired using a Leica TCS SP5 II (63× oil immersion objective; NA ¼ 1.4) and were scanned sequentially to minimize fluorophore cross-talk and false-positive colocalization." And the rabbit techniques were also adapted from Zhou et al: "Animal studies and welfare In vivo xenografted tumor models and pharmacodynamic studies were carried out as described before. All experimental protocols were approved by Agensys' Institutional Animal Care and Use Committee. All procedures in the toxicology studies were in compliance with the Animal Welfare Act and Regulations (9 C.F.R. 3). Male Dutch Belted [Haz:(DB) SPF] rabbits weighing approximately 1.5 to 2.0 kg were used for ocular tolerability studies. Rabbits were acclimated for at least 6 days prior to first dose. All animals were housed in individual, suspended, stainless steel caging, were provided feed and water, and were maintained under environmental conditions in compliance with all animal welfare guidelines. Test articles were administered to groups of 3 to 4 rabbits intravenously via a marginal ear vein, followed by a saline flush once weekly for up to six doses (days 1, 8, 15, and 22). General health was assessed by weekly measurement of body weight and cage-side observations. Ocular tolerability was assessed by external examination—slit lamp biomicroscopy to examine the adnexa and anterior portion of each eye. In addition, the ocular fundus was examined using an indirect ophthalmoscope following dilation with a mydriatic agent. Corneal fluorescein staining was also performed to examine corneal damage. A fluorescein solution (approximately 1 mg/mL) was applied to the cornea by a cotton-tipped swab. At necropsy, eyes and other selected tissues were placed in fixative according to established procedures for IHC. All rabbit studies were performed by Covance Laboratories." Standard statistical approaches are utilized in the results calculations.

All references, publications, and patents are incorporated herein in their entirety.

EXAMPLES

Results show significant benefit of the primary endpoint and for multiple secondary analyses.

All animal experiments are conducted in accordance with policies of the NIH Guide for the Care and Use of Laboratory Animals and the Institutional Animal Care and Use Committee (IACUC). Specific protocols are approved by appropriate review boards.

These experimental results, all or in part, demonstrate the utility of the invention. If data is contradictory, as scientific data is sometimes want to be, a physical benefit is demonstrated through a variation of experimental conditions that appropriately isolate key variables.

In all examples, target cell safety is maintained in the presence of the copolymer. The human and mammal formulations are well tolerated.

Example 1

Respiratory epithelial cells in culture and with the presence of a SARS-CoV-2 viral particles leads to very high infectivity rates of these cells and their subsequent demise. When a cationic graft co-polymer is added in solution to this system, at concentrations of 0.001, 0.01, 0.1, 1, 2, and 3% w/w for long enough to allow significant infection rates, for example hours. The viral infectivity is reduced and cell survival is enhanced, on a dose response basis. The negative control is solution only with lack of any cationic graft copolymer. There are multiple experiments performed to show this beneficial effect. One involves cell survival as measured with a cytometer, another involves quantitative PCR to measure the number of copies of the viral genome. In one experiment, viable respiratory epithelial cells are counted in solution to provide a #live respiratory epithelial cells/ml. PLL (20)-g[3.5]-PEG(5) is added as a lyophilized powder in different amounts to provide the concentrations tested into the various wells and cell cultures (standard growth and survival media). The same amount of SARS-CoV-2 viral particles, at an absolute viral particle numbers per well, is added. After 24 hours cell viability is counted. Experimentation prior shows the best number of viral particles to add. Empiric data suggests 10,000 viral particles per ml is effective at infecting the respiratory cells with the majority of cultured cells in the well dying at 24 hours. The solutions containing PLL-g-PEG showed improved cell survival as shown below in Table 1.

TABLE 1

| | Respiratory cell survival | Conclusion |
|---|---|---|
| Concentration PLL-g-PEG % on a w/w basis in presence of SARS-Cov-2 | | |
| None (negative control) | lowest seen | Standard control result |
| 0.001 | slightly improved vs. control | Evidence of efficacy |

TABLE 1-continued

| | Respiratory cell survival | Conclusion |
|---|---|---|
| 0.01 | improved vs. control | Effective |
| 0.1 | improved vs. control | Effective |
| 1 | improved vs. control | Effective |
| 3 | improved vs. control | Effective |

Another method to demonstrate the same effectiveness of the intervention with a cationic graft copolymer in the setting of SARS-Cov-2 infection is performed using a similar design, except the endpoint is RNA copies of the viral genome. In this experiment, the same PLL-g-PEG concentrations are used, but the cells are washed from all viral media and PLL-g-PEG media after exposure and a 2-hour incubation period. 24 hours later the solutions are tested for viral RNA copies. Detection of the SARS-CoV-2 virus is performed using the One Step Prime Script RT-PCR kit on the Light Cycler 480 Real-Time PCR system with primers. The following sequences are used: forward primer: 5'-AGAAGATTGGTTAGATGATGATAGT-3; reverse primer:5'-TTCCATCTCTAATTGAGGTTGAACC-3; and probe:5'-FAM-TCCTCACTGCCGTCTTGTTG ACCA-BHQ1-3'. All experiments are conducted in triplicates. Table 2 shows these results.

TABLE 2

| | RNA viral copies (qualitative) | Conclusion |
|---|---|---|
| Concentration PLL-g-PEG % on a w/w basis in presence of SARS-Cov-2, prior to transition to pure media | | |
| None (negative control) | Most | Standard control result |
| 0.001 | Fewer | Evidence of efficacy |
| 0.01 | Fewer | Effective |
| 0.1 | Fewer | Effective |
| 1 | Fewer | Effective |
| 3 | Significantly fewer | Effective |

These studies are conducted with enough well plates (triplicates) to demonstrate statistical significance. This experiment reduces to practice the specific opportunity with the utilization of cationic graft copolymers to reduce SARS-CoV-2 viral infectivity into at risk cells, and hence, tissues and organisms.

Example 2

A clinical study is conducted to demonstrate the clinical benefit of this invention. Humans at risk for SARS-CoV-2 viral infection (COVID19) are treated with topical formulations of PLL-g-PEG. These formulations are liquid based. A person at risk for SARS-CoV-2 viral infection based on high-risk exposure through a workplace environment is enrolled in the trial. 1000 patients are enrolled in a 1:1:1 randomization schema. The study is double masked. Dose A is PLL-g-PEG as follows: eye drop 0.1%, Nasal spray 0.1%, and oral rinse 0.1%; Dose B is eye drop 0.5%, Nasal spray 0.5%, and oral rinse 0.5%. Cohort C receives saline only via eye drop, nasal spray and oral rinse. Participants are stratified equally by sex, age (>60, <60) and as front-line emergency medical providers in acute care high volume COVID19 hospital settings or police officers and emergency medical technician first responders to medical calls. At enrollment all participants are Sars-Cov-2 negative and are provided with the solutions for use. Instructions are to apply to ocular, nasal, and oral mucosa just prior to entering the at-risk environment. Applications must be repeated every four hours as needed based on exposure risk. Standard precautions are utilized in addition to the PLL-g-PEG formulations or saline. Duration of study is two weeks of treatment or control. The endpoints assessed at 4 weeks include is number of A) infected study subjects following initiation of therapy or control and B) severity of illness on a grade of 1-resolved without hospitalization, 2-hospitalization required, 3-ICU required or death. As a substudy, swabbing demonstrated statistically equivalent amounts of viral particles on the patient's personal protective equipment and on inanimate object surfaces such as the counter and bedside table in the room. The person at risk for infection, practices personal safety precautions, but despite this, the exposure of the at-risk person's mucous membranes is significant. Infection of the at-risk person is prevented because the use of the cationic graft copolymer formulations, showing reduction in infection rates and disease severity.

Table 3 shows results.

TABLE 3

| | Infections COVID19 | Mean severity of infections |
|---|---|---|
| Concentration PLL-g-PEG % formulations on a w/w basis in study participants | | |
| None (negative control) | many | most |
| 0.1 | fewer | reduced |
| 0.5 | fewer | reduced |
| 1 | Lower than 0.5% dose infection | reduced |

Note for the in vivo and in vitro experiments use of the text and design from Zhou et al is utilized.

Example 3: ADC In Vitro

An ADC is AGS-16C3F: AGS-16C3F is an antibody—drug conjugate against ectonucleotide pyrophosphatase/phosphodiesterase 3 (ENPP3)containing the mcMMAF linker-payload for treatment of metastatic renal cell carcinoma. AGS-16C3F or Rituxumab-mcMMAF as a test article (an ADC that binds CD20) or other ADCs may be used.

Other ADCs have been reported to cause ocular toxicity in patients by mechanisms for which understanding is just developing. This invention represents an approach based on experimentation and new ideas about this toxicity.

Human primary corneal epithelial cells are cultured in keratinocyte-SFM and HCEC cells from ATCC are cultured in corneal epithelial cell basal medium supplemented with corneal epithelial cell growth kit.

Human cell lines are confirmed utilizing short tandem repeat profiling and confirmed to be *Mycoplasma* negative. Cells are seeded onto multiple 8-well chamber slides and cultured for 48 hours prior to treatment and subsequent immunostaining. Cells are treated with a negative control (no copolymer) and also simply PLL and PEG (not grafted together). The other cell cultures are exposed to PLL-g-PEG (PLL(20-g[3.5[-PEG(5)) as prime example. Other PLL-g-PEGs are tested similarly. PLL-g-PEG concentrations are 0.001, 0.01, 0.1, 0.3, 0.5, and 1% w/w. Keratocytes are able to maintain viability after treatment with PLL-g-PEG, but in the setting of an in vitro experiment some keratocytes may die in the experiment. Keratocytes are then incubated with AGS-16C3F (or Rituxumab-mcMMAF or another ADC) with and without coincubation of 0.5 mg/mL Dextran-Texas Red for 4 hours at 37 C. Inhibition of macropinocytosis as a control is evaluated by treating cells with EIPA for 30 minutes prior to AGS-16C3F (or other ADC)/Dextran-Texas Red incubation. After the incubation period, unbound antibody and copolymer is washed off with PBS and cells are fixed in 4% paraformaldehyde for 20 minutes at room temperature. Cells are then permeabilized in PBS plus 0.1% Triton-X-100 for 15 minutes, and nonspecific labeling is blocked in PBS plus 10% normal goat serum. Cell surface—bound and internalized cytosolic AGS-16C3F (or other ADC) is visualized by incubating cells with Alexa Fluor 488—labeled goat anti-human IgG. Nuclei are visualized with TO-PRO-3 Iodide, and coverslips are mounted using ProLong Gold Antifade reagent for imaging. High-resolution laser confocal image sections are acquired using a Leica TCS SP5 II (63× oil immersion objective; NA ¼ 1.4) and are scanned sequentially to minimize fluorophore cross-talk and false-positive colocalization.

ADCs (2 mg/mL or other concentrations) are prepared in PBS, and 1:2 serial dilutions are made in a black-walled, 96-well plate (21, 23). Equal volume of 1,8-ANS is added and incubated for 30 minutes at room temperature. Fluorescence signal is measured.

Results:

Upon microscopy, many fewer stained ADC's entered copolymer treated epithelial cells. A dose response is exhibited.

The models are used, and design as well, but no idea or intellectual property was, is, or has been obtained from Zhou or any other authors of references cited.

See Table 4.

TABLE 4

| Concentration PLL-g-PEG % formulations on a w/w basis in study arms | Intracellular uptake by staining experiment |
|---|---|
| None (negative control) | High |
| None (PLL and PEG not grafted together) | High |
| 0.001 | Relatively less to no difference |
| 0.01 | Less than negative control |
| 0.1 | Less than negative control |
| 0.5 | Less than negative control |
| 1 | Significantly less than negative control |

Thus, PLL-g-PEG and by extension mimetics are an effective intervention for reducing ADC related corneal toxicity.

Experiments on megakaryocytes and using mimetics are also effective.

Experiments with ADC's and tubulin disruptors and other cytotoxins are carried out and this benefit is not limited to one type of ADC. In fact, any ADC with corneal epithelial toxicity is amenable to relief with this approach. This approach is not ADC dependent and is a method to reduce this class effect corneal toxicity.

The PLL-g-PEG can also be added slightly after the ADC is added to solution, so in some embodiments benefit remains if ADC exposure is prior to PLL-g-PEG exposure.

Example 4: ADC In Vivo

ADC related corneal toxicity is reduced in in vivo models. Although animal models in ADC toxicity are imperfect (cynomolgus models are not optimal), rabbits are commonly used to test possible drug-mediated eye toxicities and are chosen to investigate the ocular toxicity of ADCs. AGS-16C3F and other ADCs are useful in these experiments. In vivo animal toxicity, although very prevalent in the human, is somewhat variable as a model in the animal. The rabbit shows varying toxicity to various ADCs. For this experiment, multiple ocular studies testing AGS-16C3F (AGS-16C3F is an antibody—drug conjugate against ectonucleotide pyrophosphatase/phosphodiesterase 3 (ENPP3) containing the mcMMAF linker-payload for treatment of metastatic renal cell carcinoma) and other ADCs with tubulin inhibiting payloads are carried out in rabbits. Five animals in each group are dosed. There is a non-ADC dosed control arm that shows no toxicity in any anuAGS-16C3F at 10- and 15-mg/kg doses are used and show ADC toxicity. Rabbits dosed at 15 mg/kg show reversible conjunctival hyperemia, perilimbal corneal haze, corneal edema, and ciliary flush. Likewise, the 10-mg/kg once-weekly dose causes ophthalmologic toxicity as well. Versus no exposure to PLL-g-PEG via topical treatment at the initiation of ADC dosing, the rabbit eyes of those treated with topical PLL-g-PEG eye drops dosed three times daily at 0.5%, 1% and 2% show reduced toxicity in this experiment. On average the benefit is >5%, >7.5%, and >10% better in the PLL-g-PEG dosed groups, 0.5%, 1%, and 2%, respectively. Dosing is daily with the PLL-g-PEG eye drop and control. ADC infusion is weekly. A beneficial effect is also seen when the PLL-g-PEG is administered beginning one week after dosing with ADC, although the benefit is reduced by approximately 20% in each group at end of experiment. PLL-g-PEG treated animals have fewer ADC related toxicities versus control (artificial tears only). All formulations are preservative free. Preserved formulations are effective but have the unwanted effects of causing or exacerbating a corneal epitheliopathy, nevertheless, in a rabbit model benefit is shown even using preserved solutions.

Subconjunctival formulations are also protective when delivered subconjunctivally once weekly.

Intravenous formulations are safe and acceptable and efficacious; however, local delivery is more efficacious.

Results are documented through exam findings (including staining) and histopathology at Days 21 and 42 (fewer infiltrates and tissue damage).

The use of PLL-g-PEG solutions improves recovery time in treated animals.

Other experiments with alternative polymer configurations are effective.

Note that the rabbit findings do not replicate human pyknotic findings identically, but the model demonstrates anterior corneal abnormalities both clinically and on histopathology. Sample ADC's selected, results are repeated with other ADC's with tubulin inhibitors.

See Table 5

TABLE 5

| Concentration % PLL-g-PEG formulations on a w/w basis in animal groups treated with AGS-163CF | Examination findings | Inflammation by histopathology |
|---|---|---|
| None (negative control) | Significant corneal staining | Significant inflammatory cells |

TABLE 5-continued

| | | |
|---|---|---|
| 0.5 | Decreased staining | Reduced inflammation |
| 1 | Decreased staining | Reduced inflammation |
| 2 | Decreased staining | Reduced inflammation |

Example 5: ADC in Humans

This study is run in patients being prescribed ADC's for oncologic disease using ADC's with known corneal toxicity. Commercially available ADC's are utilized in a clinical care setting for approved ADC's, as are patients receiving not yet approved ADC's under clinical investigations as part of the regulatory approval process. Thus, this randomized controlled trial is performed in patients on multiple different ADC's; stratification is by ADC and pre-existing eye discomfort. 75 patients are enrolled as it is determined empirically this total N with 25 subjects per arm is sufficient to detect a difference in eye findings.

All patients are enrolled at the initiation of therapy. Patients are randomized to preservative free artificial tears only, 1% PLL-g-PEG eye drops (unpreserved, and 2% PLL-g-PEG eye drops (unpreserved). All patients are instructed to use the drops in both eyes four times per day starting one day before Cycle 1 ADC dosing. Eye exams are performed at Baseline and at every Cycle through Cycle 4. One Cycle is 21 days. After Cycle 4, patients are allowed to stay on PLL-g-PEG if they are enrolled into a treatment arm. Those randomized to artificial tears are allowed to cross-over to PLL-g-PEG eye drops.

The extent of corneal microcyst-like epitheliopathy or superficial punctate keratitis or keratopathy is assessed using an objective analysis estimating the density and region of the epitheliopathy and/or assessments of epithelial injury by staining with vital dyes such as fluorescein. A score based on percent of cornea involved multiplied by a correction factor of overall clinical severity (1 to 3) is used. The study endpoint is most severe score over study duration.

Visual acuity is also measured in logMAR.

For the primary analysis, the worst eye is used per patient.

Eyes are also looked at independently.

Adverse events recorded.

Improvement of symptoms is assessed for the cross over group.

Results follow:

TABLE 6

Study results Clinical trial in reducing epithelial keratopathy AEs ay worst time point

| Dose Group | Microcyst like score | LogMAR BCVA |
|---|---|---|
| Control | highest | impaired vision |
| 1% PLL-g-PEG | Lower | mildly less impaired vision |

TABLE 6-continued

Study results Clinical trial in reducing epithelial keratopathy AEs ay worst time point

| Dose Group | Microcyst like score | LogMAR BCVA |
|---|---|---|
| 2% PLL-g-PEG | Lower | mildly less impaired vision |

Adverse events of blurred vision and ocular irritation are highest in controls, and lower in low dose and high dose.

Dose holds and dose delays in each group is highest in controls, and lower in low dose and high dose.

PLL-g-PEG treated eyes show less corneal superficial punctate keratitis. Visual acuity is better, on average, in PLL-g-PEG (or copolymer) treated eyes and patients.

This experiment reveals, by example, the clinical value of this intervention with PLL-g-PEG solution used topically on the eye to reduce the adverse corneal effects of ADCs.

A concomitant intravenous delivery of a 1% PLL-g-PEG solution at each cycle of dosing shows less thrombocytopenia in treated subjects, thereby demonstrating the broader effect of mitigating ADC toxicity to systems that extend outside the corneal epithelium, thus supporting broader claims.

These experiments are repeated successfully with other copolymers.

Example 7

When a variety of novel ADC's are assessed preclinically for uptake into a human corneal epithelial cell in the presence of PLL-g-PEG formulations, then those specific ADC's that show greatest benefit (most reduced uptake) in the presence of PLL-g-PEG can be advanced into the clinic. One reason for a selection is there is now a known and effective clinical method to treat, mediate, mitigate, reduce, and prevent ADC toxicity in that cell type with co-treatment with copolymers claimed and discussed herein Three variations of ADC's that target the cell receptor found in an oncologic disease with unmet need are assessed in the lab. All show significant macropinocytotic uptake into human corneal epithelial cells. PLL-g-PEG solutions of varying concentration (range 0.01 to 3% weight/weight are then used in a similar test of human epithelial cell ADC uptake in vitro. Assessments of the potential toxicity of ADC's is reassessed. PLL-g-PEG at 0.01% or higher (not necessarily inclusive) is found to significantly reduce the uptake of one of the three ADC's in vitro at a percentage that may vary based on ADC, but is still effective. This effect is confirmed in a rabbit in vivo model. The molecule is thus advanced to the clinic ahead of the others as there is a known method to minimize uptake with locally applied PLL-g-PEG. Other bioadhesive/passivation copolymers are used in ADC development in a similar manner as the experiments described above.

What is claimed is:

1. A method to decrease an ocular adverse event(s) in a patient undergoing antibody-drug conjugate therapy, where said adverse event(s) comprise damage to nonneoplastic cells, the method comprising applying to said patient a copolymer in an amount and a time effective to decrease said damage or adverse effects to said nonneoplastic cells, wherein said copolymer is poly(L-lysine)-graft-poly(ethylene glycol) (PLL-g-PEG), wherein said step of applying said copolymer to said patient decreases said damage or adverse effects to said nonneoplastic cells, wherein said ocular adverse event is corneal epithelial toxicity associated with antibody-drug conjugate therapy, and and wherein said copolymer is applied to corneal and conjunctival epithelial cells of said patient in an amount and a time effective to decrease corneal epithelial toxicity associated with said antibody-drug conjugate therapy in said patient.

2. The method of claim 1, wherein said copolymer is applied to corneal epithelial cells at risk of antibody-drug conjugate (ADC) uptake.

3. The method of claim 1, wherein said step of applying said copolymer to said patient is prior to initiation of systemic antibody-drug conjugate therapy in said patient.

4. The method of claim 1, wherein said step of applying said copolymer to said patient is after initiation of systemic antibody-drug conjugate therapy in said patient, wherein applying said copolymer decreases symptoms of ocular adverse events associated with the antibody-drug conjugate therapy in said patient.

5. The method of claim 1, wherein said copolymer is applied to the eye of said patient, optionally as an eye drop formulation, in an amount and for a time effective to reduce the number of dose holds and dose reductions of antibody-drug conjugates in the treatment of human malignancy, thereby reducing corneal adverse events and ocular safety concerns, in an at-risk patient.

6. A method to decrease an ocular adverse event(s) in a patient undergoing monoclonal antibody therapy, wherein said adverse event(s) comprise damage to the corneal epithelium, said method comprising:

applying a copolymer to said patient in an amount and for a time effective to decrease said damage or adverse effects to the corneal epithelium, wherein said copolymer is poly(L-lysine)-graft-poly(ethylene glycol) (PLL-g-PEG), wherein said ocular adverse event(s) is corneal epithelial toxicity associated with monoclonal antibody therapy, wherein said step of applying said copolymer to said patient decreases said damage to the corneal epithelium, wherein said copolymer is applied to corneal and conjunctival epithelial cells of said patient in an amount and for a time effective to decrease said corneal epithelial toxicity associated with monoclonal antibody epithelial toxicity in said patient.

7. The method of claim 1, where said decrease in adverse events comprising damage to nonneoplastic cells is a numerical reduction in the adverse events comprising damage to nonneoplastic cells in said patient compared with untreated comparative patients.

8. The method of claim 7, where said numerical reduction is at least 5% compared with untreated comparative populations.

9. The method of claim 6, where said decrease in corneal epithelial toxicity is a numerical reduction in the corneal epithelial toxicity in said patient compared with untreated comparative patients.

10. The method of claim 9, where said numerical reduction is at least 5% compared with untreated comparative populations.

* * * * *

SEQUENCE LISTING

```
Sequence total quantity: 3
SEQ ID NO: 1            moltype = DNA  length = 25
FEATURE                 Location/Qualifiers
source                  1..25
                        mol_type = other DNA
                        organism = synthetic construct
SEQUENCE: 1
```

-continued

```
agaagattgg ttagatgatg atagt                                    25

SEQ ID NO: 2            moltype = DNA  length = 25
FEATURE                 Location/Qualifiers
source                  1..25
                        mol_type = other DNA
                        organism = synthetic construct
SEQUENCE: 2
ttccatctct aattgaggtt gaacc                                    25

SEQ ID NO: 3            moltype = DNA  length = 24
FEATURE                 Location/Qualifiers
source                  1..24
                        mol_type = other DNA
                        organism = synthetic construct
SEQUENCE: 3
tcctcactgc cgtcttgttg acca                                     24
```